US010488321B2

(12) United States Patent
Fathollahi et al.

(10) Patent No.: US 10,488,321 B2
(45) Date of Patent: Nov. 26, 2019

(54) DEVICES AND METHODS FOR HIGH-THROUGHPUT SINGLE CELL AND BIOMOLECULE ANALYSIS AND RETRIEVAL IN A MICROFLUIDIC CHIP

(71) Applicants: The Board of Trustees of the Leland Stanford Junior University, Stanford, CA (US); Cella Genomics Inc., Palo Alto, CA (US)

(72) Inventors: Bahram Fathollahi, Palo Alto, CA (US); Daniel G. Stearns, Palo Alto, CA (US); William Whalen, Palo Alto, CA (US)

(73) Assignees: The Board of Trustees of the Leland Stanford Junior University, Stanford, CA (US); Cella Genomics Inc., Palo Alto, CA (US)

( * ) Notice: Subject to any disclaimer, the term of this patent is extended or adjusted under 35 U.S.C. 154(b) by 100 days.

(21) Appl. No.: 15/559,380

(22) PCT Filed: Mar. 18, 2016

(86) PCT No.: PCT/US2016/023192
§ 371 (c)(1),
(2) Date: Sep. 18, 2017

(87) PCT Pub. No.: WO2016/149639
PCT Pub. Date: Sep. 22, 2016

(65) Prior Publication Data
US 2018/0067038 A1   Mar. 8, 2018

Related U.S. Application Data

(60) Provisional application No. 62/135,601, filed on Mar. 19, 2015.

(51) Int. Cl.
*B01L 3/00* (2006.01)
*G01N 15/06* (2006.01)
(Continued)

(52) U.S. Cl.
CPC .... *G01N 15/1463* (2013.01); *B01L 3/502761* (2013.01); *G01N 15/06* (2013.01);
(Continued)

(58) Field of Classification Search
CPC .......... B01L 3/00; G01N 15/06; G01N 33/00; G01N 33/48; G01N 35/00
(Continued)

(56) References Cited

U.S. PATENT DOCUMENTS 5,955,028 A * 9/1999 Chow .............. B01L 3/502715
                                                    204/600
7,686,500 B2   3/2010 Laugharn et al.
(Continued)

FOREIGN PATENT DOCUMENTS

WO   WO-2004/051266 A1   6/2004
WO   WO-2009/017226 A1   2/2009
(Continued)

OTHER PUBLICATIONS

International Preliminary Report on Patentability for International Application No. PCT/US2016/023192 dated Sep. 28, 2017, 10 pages.
(Continued)

*Primary Examiner* — Brian J. Sines
(74) *Attorney, Agent, or Firm* — Foley & Lardner LLP; Cliff Z. Liu

(57) ABSTRACT

Described here is a device comprising a microfluidic chip and an acoustic transducer external to the microfluidic chip, wherein the microfluidic chip comprises a channel in communication with a microwell having a volume less than one
(Continued)

microliter, and wherein the acoustic transducer is coupled to the microfluidic chip via a coupling medium. Also described here is a method for analyzing a cell or a biomolecule, comprising applying a focused acoustic beam to a microfluidic chip comprising a channel in fluid communication with a microwell having a volume less than one microliter, wherein the microwell comprises an aqueous compartment comprising a cell or a biomolecule, wherein the channel comprises a non-aqueous liquid phase immiscible with the aqueous compartment which encapsulates the aqueous compartment in the microwell, and wherein the acoustic beam displaces a meniscus at an interface of the aqueous compartment and the non-aqueous liquid phase thereby ejecting the aqueous compartment from the microwell into the channel as an aqueous droplet.

12 Claims, 18 Drawing Sheets

(51) Int. Cl.
*G01N 33/00* (2006.01)
*G01N 33/48* (2006.01)
*G01N 35/00* (2006.01)
*G01N 15/14* (2006.01)
*G01N 35/02* (2006.01)
*G01N 15/10* (2006.01)
*G01N 35/10* (2006.01)

(52) U.S. Cl.
CPC .... *G01N 35/028* (2013.01); *B01L 2200/0668* (2013.01); *B01L 2300/0893* (2013.01); *G01N 2015/0693* (2013.01); *G01N 2015/1006* (2013.01); *G01N 2015/1465* (2013.01); *G01N 2035/1034* (2013.01)

(58) Field of Classification Search
USPC ................... 422/68.1, 502, 503, 504; 436/43
See application file for complete search history.

(56) References Cited

U.S. PATENT DOCUMENTS

| | | | |
|---|---|---|---|
| 8,387,803 B2 | 3/2013 | Thorslund et al. | |
| 8,425,749 B1* | 4/2013 | Ravula .................... | B03C 5/026 181/141 |
| 8,445,193 B2 | 5/2013 | Muraguchi et al. | |
| 8,573,060 B2 | 11/2013 | Huang et al. | |
| 8,835,188 B2 | 9/2014 | Love et al. | |
| 2001/0045358 A1* | 11/2001 | Kopf-Sill .............. | B01L 3/5027 204/452 |
| 2002/0176804 A1* | 11/2002 | Strand ................. | B01J 19/0093 422/400 |
| 2005/0015001 A1* | 1/2005 | Lec .......................... | A61B 8/12 600/369 |
| 2006/0078946 A1 | 4/2006 | Muraguchi et al. | |
| 2007/0065808 A1 | 3/2007 | Bohm et al. | |
| 2009/0061513 A1 | 3/2009 | Andersson Svahn et al. | |
| 2009/0226994 A1 | 9/2009 | Lemor et al. | |
| 2010/0078077 A1 | 4/2010 | Ismagilov et al. | |
| 2011/0111981 A1 | 5/2011 | Love et al. | |
| 2011/0124098 A1* | 5/2011 | Rose ................. | B01L 3/502753 435/306.1 |
| 2011/0124520 A1 | 5/2011 | Love et al. | |
| 2011/0281743 A1 | 11/2011 | Allbritton et al. | |
| 2012/0149592 A1 | 6/2012 | Love et al. | |
| 2013/0213488 A1 | 8/2013 | Weitz et al. | |
| 2014/0113838 A1 | 4/2014 | Folch et al. | |
| 2014/0262787 A1 | 9/2014 | Molho et al. | |
| 2014/0376816 A1 | 12/2014 | Lagae et al. | |
| 2015/0219623 A1* | 8/2015 | Doria ................ | B01L 3/502761 435/29 |

FOREIGN PATENT DOCUMENTS

| | | |
|---|---|---|
| WO | WO-2010/040831 A1 | 4/2010 |
| WO | WO-2013/188872 A1 | 12/2013 |
| WO | WO-2014/142924 A1 | 9/2014 |

OTHER PUBLICATIONS

International Search Report and Written Opinion (ISA/KR) for International Application No. PCT/US2016/023192, dated Jun. 24, 2016.

* cited by examiner d=50 um  S=100 um  NW017

DEVICES AND METHODS FOR HIGH-THROUGHPUT SINGLE CELL AND BIOMOLECULE ANALYSIS AND RETRIEVAL IN A MICROFLUIDIC CHIP

CROSS-REFERENCE TO RELATED APPLICATIONS

This application is a national stage entry under 35 U.S.C. § 371 of International Application No. PCT/US2016/023192, filed Mar. 18, 2016, which claims the benefit of U.S. Provisional Patent Application No. 62/135,601 filed Mar. 19, 2015, the content of each of which is hereby incorporated herein by reference in its entirety.

BACKGROUND

Single cell analysis (SCA) is an active area of research and commercial development for determining cellular heterogeneity and monitoring cellular functions. Single cell applications focus on classification of subpopulation based on immunophenotyping or sequencing of genomic content. Clinical applications of SCA include the screening for rare cells, for example circulating tumor cells (CTCs), in an enriched sample.

Current methods for cell isolation include limiting dilution using large liquid handler instruments, flow cytometry, and laser capture microdissection (LCM). Flow cytometry is a high throughput sorting method but is typically limited to single time point analysis, large downstream volumes, and high shear flow that can lower cell viability and limit to certain cell types. Limiting dilution and LCM are labor intensive and in the case of LCM low throughput. Microfluidic platforms are addressing the automation need for single cell isolation and sample preparation for gene expression studies by real-time PCR or sequencing but are typically limited to 100 cells or less. Droplet based microfluidics is capable of addressing both automation and high throughput needs but sequential reagent addition is typically not possible after encapsulation and downstream sorting may be required. Microwell arrays have also been used for isolation of single cells. However, microwell array platforms typically rely on manual addition of reagents and use of a micropipette for retrieval of contents from microwell arrays.

In addition, an alternative method to quantitative polymerase chain reaction (qPCR) is digital PCR. In digital PCR, the reaction mixture is compartmentalized in microchambers such as microwells or in monodisperse droplets (droplet digital PCR). The advantages of digital PCR over qPCR include precision and sensitivity. Although there are several commercialized digital PCR instruments currently available that are based on droplets or microchambers, current platforms typically are not fully integrated or typically lack the capability to retrieve the positive samples for downstream processing.

A need exists for innovative technologies that can integrate and automate single cell isolation, screening, and retrieval at increased throughput in a single experiment. A further need exists for a digital PCR platform with the integrated capability to retrieve positive samples for downstream processing.

SUMMARY

Described here is an automated high throughput method for spatial isolation of single-cells or biomolecules (e.g., nucleic acids such as DNA and RNA, proteins, peptides, other biomolecules or particles) in a microfluidic chip comprising microwell arrays, image-based screening of the isolated cells or biomolecules, and retrieval of selected single cells or its contents or selected biomolecules by extrinsic actuation for downstream processing. Screening can include the detection of fluorescent reporters that identify unique protein markers, amplification of target nucleic acids, genomic amplification of lysed cells, or cellular response to stimulus. The method allows the detection of subsets or rare cells within a heterogeneous cell population that can be retrieved for downstream processing including genomic sequencing. The method further allows the detection and retrieval of positive digital PCR amplification products for downstream processing such as next generation sequencing.

One aspect of some embodiments of the disclosure relates to a device comprising a microfluidic chip and an acoustic transducer configured to apply an acoustic beam to the microfluidic chip, wherein the microfluidic chip defines a microwell having a volume less than one microliter and a channel in communication with the microwell. In some embodiments, the acoustic transducer is external to the microfluidic chip rather than integrated within the microfluidic chip. In some embodiments, the acoustic transducer is configured to apply an acoustic beam to the microfluidic chip via a coupling medium. In some embodiments, the device comprises a container or housing configured to accommodate the coupling medium.

In some embodiments, the microwell has a volume configured to receive a single cell. In some embodiments, the microwell has a volume of about 100 nanoliters or less, or about 10 nanoliters or less, or about 1 nanoliter or less, or about 500 picoliters or less, or about 200 picoliters or less, or about 100 picoliters or less.

In some embodiments, the microfluidic chip comprises at least about 100 microwells, or at least about 1,000 microwells, or at least about 10,000 microwells, or at least about 100,000 microwells, or up to about 1,000,000 microwells. The array of microwells can be uniform in volume or can be varying in volume on a microfluidic chip.

In some embodiments, the device further comprises an actuator configured to translate the microfluidic chip laterally with respect to the acoustic transducer, so as to aim the acoustic transducer at different microwells. In some embodiments, the device further comprises an actuator configured to translate the microfluidic chip vertically with respect to the acoustic transducer, so as to focus or defocus the acoustic transducer.

In some embodiments, the microfluidic chip is substantially or totally free of a built-in transducer.

In some embodiments, the acoustic transducer is configured to operate at a frequency of about 1-30 MHz, or at a frequency of about 1-10 MHz, or at a frequency of about 10-20 MHz, or at a frequency of about 20-30 MHz.

In some embodiments, the acoustic transducer is configured to apply a focused acoustic beam on a spot having a size of about 25-200 µm, or about 25-50 µm, or about 50-100 µm, or about 100-200 µm, within the microwell.

In some embodiments, the coupling medium comprises water. In some embodiments, the coupling medium comprises an aqueous gel.

In some embodiments, the device further comprises an imaging system configured to image the microwell. In some embodiments, the microfluidic chip defines a first side and a second side, wherein the acoustic transducer is positioned at the first side, and the imaging system is positioned at the second side.

In some embodiments, the microfluidic chip comprises an aqueous compartment comprising a cell or a biomolecule disposed in the microwell, and a non-aqueous liquid phase substantially immiscible with the aqueous compartment disposed in the channel which encapsulates the aqueous compartment in the microwell. In some embodiments, the non-aqueous liquid phase comprises a hydrocarbon oil, a fluorocarbon oil, or a silicone oil. In some embodiments, the acoustic transducer is configured to apply a focused acoustic beam to displace a meniscus at an interface of the aqueous compartment and the non-aqueous liquid phase.

Another aspect of some embodiments of the disclosure relates to a method for analyzing a cell or a biomolecule (e.g., nucleic acids such as DNA and RNA, proteins, other biomolecules or particles), comprising applying a focused acoustic beam to a microfluidic chip defining a microwell having a volume less than one microliter and a channel in fluid communication with the microwell, wherein the microwell comprises an aqueous compartment comprising a cell or a biomolecule, wherein the channel comprises a non-aqueous liquid phase substantially immiscible with the aqueous compartment which encapsulates the aqueous compartment in the microwell, and wherein the acoustic beam displaces a meniscus at an interface of the aqueous compartment and the non-aqueous liquid phase thereby ejecting the aqueous compartment from the microwell as an aqueous droplet into the channel.

In some embodiments, the non-aqueous liquid phase comprises an oil. In some embodiments, the non-aqueous liquid phase comprises a fluorocarbon oil. In some embodiments, the non-aqueous liquid phase comprises FC-40 or Novec 7500. In some embodiments, the non-aqueous liquid phase further comprises a surfactant in the fluorocarbon oil.

In some embodiments, the acoustic beam is applied by an external acoustic transducer operating at a frequency of about 1-30 MHz, or at a frequency of about 1-10 MHz, or at a frequency of about 10-20 MHz, or at a frequency of about 20-50 MHz.

In some embodiments, the acoustic beam focuses on a spot having a size of about 25-200 µm, or about 25-50 µm, or about 50-100 µm, or about 100-200 µm, within the microwell.

In some embodiments, the method further comprises compartmentalizing the aqueous sample in the microwell before applying the acoustic beam. In some embodiments, a sample suspension containing cells of optimized density or biomolecules or particles is introduced into the microfluidic chip by flow and compartmentalized in the microwells. In some embodiments, vacuum pressure is applied for a few minutes to remove trapped air in microwells followed by exposure to atmospheric pressure to flow the suspension into the evacuated chip in order to rapidly compartmentalize the aqueous sample within the microwells. In some embodiments, pressure is applied to flow the suspension over the microwell arrays and allow the cells or particles to settle into the microwells over a period of time. Cells or particles remaining outside of the microwells can be removed by flowing wash buffer solution.

In some embodiments, the method further comprises imaging the microwell before and/or after applying the acoustic beam.

The method allows capability to add reagents to microwells by introducing an aqueous flow into the microfluidic chip. Reagents can include fluorescent dyes, lysis buffer, functionalized microbeads, and amplification reagent.

The method allows image-based screening of fluorescent signal from microwells to perform single cell genomic and proteomic characterization.

The method allows lysing of single cells by directly adding reagents or in some cases applying elevated temperatures.

The method allows amplification of genomic content in microwells containing lysed single cells. This can be performed at elevated isothermal temperature or thermal cycling.

The method allows active control of the temperature of the microwells by modulating the temperature of the acoustic coupling medium.

In some embodiments, the method further comprises translating the microfluidic chip laterally with respect to the acoustic transducer to select microwells. In some embodiments, the method further comprises translating the microfluidic chip vertically with respect to the acoustic transducer to adjust focus of the acoustic beam.

In some embodiments, the method further comprises isolating the aqueous droplet ejected into the channel, such as by controlling the flow of the non-aqueous phase.

In some embodiments, the method further comprises applying a defocused acoustic beam to the microfluidic chip to block the movement of the ejected aqueous droplet in the channel, whereas the flow of the non-aqueous phase is not blocked. In some embodiments, the method further comprises applying a defocused acoustic beam to the microfluidic chip to deflect the ejected aqueous droplet at a channel junction.

In some embodiments, the method is substantially or totally free of the application of a surface acoustic wave. In some embodiments, the method is substantially or totally free of the use of a built-in acoustic transducer of the microfluidic chip. In some embodiments, the method is substantially or totally free of the application of a surface acoustic wave from a built-in acoustic transducer of the microfluidic chip. In some embodiments, the propagation direction of the acoustic wave is substantially not in the plane of the microfluidic channel. In some embodiments, the propagation direction of the acoustic wave is substantially perpendicular to the plane of the microfluidic channel. In some embodiments, the propagation direction of the acoustic wave is at an angle with respect to the plane of the microfluidic channel that is within a range of about $90\pm45°$, or about $90\pm400$, or about $90\pm350$, or about $90\pm300$, or about $90\pm25°$, or about $90\pm20°$, or about $90\pm15°$, or about $90\pm100$, or about $90\pm5°$.

Another aspect of some embodiments of the disclosure relates to a method for digital PCR, comprising amplifying at least one nucleic acid by PCR in a plurality of microwells; identifying at least one positive microwell by screening fluorescent signals from the microwells; and applying an acoustic beam to eject an aqueous droplet comprising the amplified nucleic acid from the positive microwell.

In some embodiments, the method comprises applying a focused acoustic beam to a microfluidic chip defining a plurality of microwells each having a volume less than one microliter and a channel in fluid communication with the microwells, wherein the microwell comprises an aqueous compartment which comprises a nucleic acid sample and a PCR reaction mixture, wherein the channel comprises a non-aqueous liquid phase substantially immiscible with the aqueous compartment which encapsulates the aqueous compartment in the microwell, and wherein the acoustic beam displaces a meniscus at an interface of the aqueous compartment and the non-aqueous liquid phase thereby ejecting the aqueous compartment from the positive microwell into the channel as an aqueous droplet.

In some embodiments, the method further comprises compartmentalizing an aqueous sample comprising a nucleic acid sample in the microwell before the amplifying step.

In some embodiments, the method further comprises adding PCR amplification reagents to the nucleic acid sample before compartmentalizing in the array of microwells.

In some embodiments, the method further comprises imaging the microwell after the amplifying step and quantifying the fluorescent signals therefrom, and optionally comparing the quantified fluorescent signals to a control to identify the positive microwell comprising the amplified nucleic acid.

In some embodiments, the ejected aqueous droplet comprising the amplified nucleic acid is isolated for further analysis such as next-generation sequencing.

A further aspect of some embodiments of the disclosure relates to method for liquid handling, comprising applying a focused acoustic beam to an interface of a first liquid phase and a second liquid phase substantially immiscible with the first liquid phase, wherein the focused acoustic beam displaces a meniscus at the interface triggering movement of the first liquid phase.

In some embodiments, the method comprises applying the acoustic beam to a microfluidic device comprising two or more immiscible fluids that are in contact at an interface. An acoustic field, generated by an external transducer, can be applied to the region surrounding the interface. A differential pressure can be induced at the interface due to the difference in acoustic energy density in the two fluids. The pressure can result in a force that can be used to modulate the position of the interface. The modulation of the interface can be restricted to a localized region by using a focused acoustic beam, and can be modulated in time by gating the acoustic beam.

In some embodiments, the method comprises actuating an liquid droplet in a two-phase microfluidic device that comprises an immiscible carrier fluid as the second liquid phase. In some embodiments, the method comprises actuating an aqueous droplet in a two-phase microfluidic device that comprises an immiscible nonaqueous liquid phase. In some embodiments, the method comprises actuating an aqueous droplet in a two-phase microfluidic device that comprises fluorocarbon oils as the second liquid phase.

In some embodiments, the method further comprises actuating an liquid droplet in a two-phase microfluidic device that comprises an immiscible carrier fluid as the second liquid phase, by using the acoustic beam to trap a droplet. This can be achieved by defocusing the beam in the microfluidic channel. The interference between the incident acoustic wave and the acoustic wave reflected from the floor of the channel can create an interference pattern of concentric nodes and antinodes. A droplet can be trapped in an antinode of this interference pattern. The droplet can then be moved in the channel by translating the acoustic actuator with respect to the microfluidic device. In this case the acoustic beam can be effectively an acoustic tweezer to provides a means for non-contact manipulation of a single droplet in a microfluidic network.

In some embodiments, the method further comprises actuating an liquid droplet in a two-phase microfluidic device that comprises an immiscible carrier fluid as the second liquid phase, by applying an acoustic beam as a valve to block the flow of the droplet in a microfluidic channel while allowing the carrier fluid to flow unimpeded. In some embodiments, the force applied to the droplets by the acoustic beam can act as a dam, causing the droplets to pile up in front of the beam, while the droplets can flow through the channel when the beam is turned off.

In some embodiments, the method further comprises actuating an liquid droplet in a two-phase microfluidic device that comprises an immiscible carrier fluid as the second liquid phase, by applying an acoustic beam to deflect droplets at a channel junction. In the absence of the acoustic beam, the droplet can flow exclusively to one channel. When the acoustic beam is turned on the resulting force can cause the droplet trajectory to flow into the other channel. The modulation of the acoustic beam can be used to sort the droplets into two (or more) output channels.

These and other features, together with the organization and manner of operation thereof, will become apparent from the following detailed description when taken in conjunction with the accompanying drawings.

DETAILED DESCRIPTION

Platform.

Figure 1:
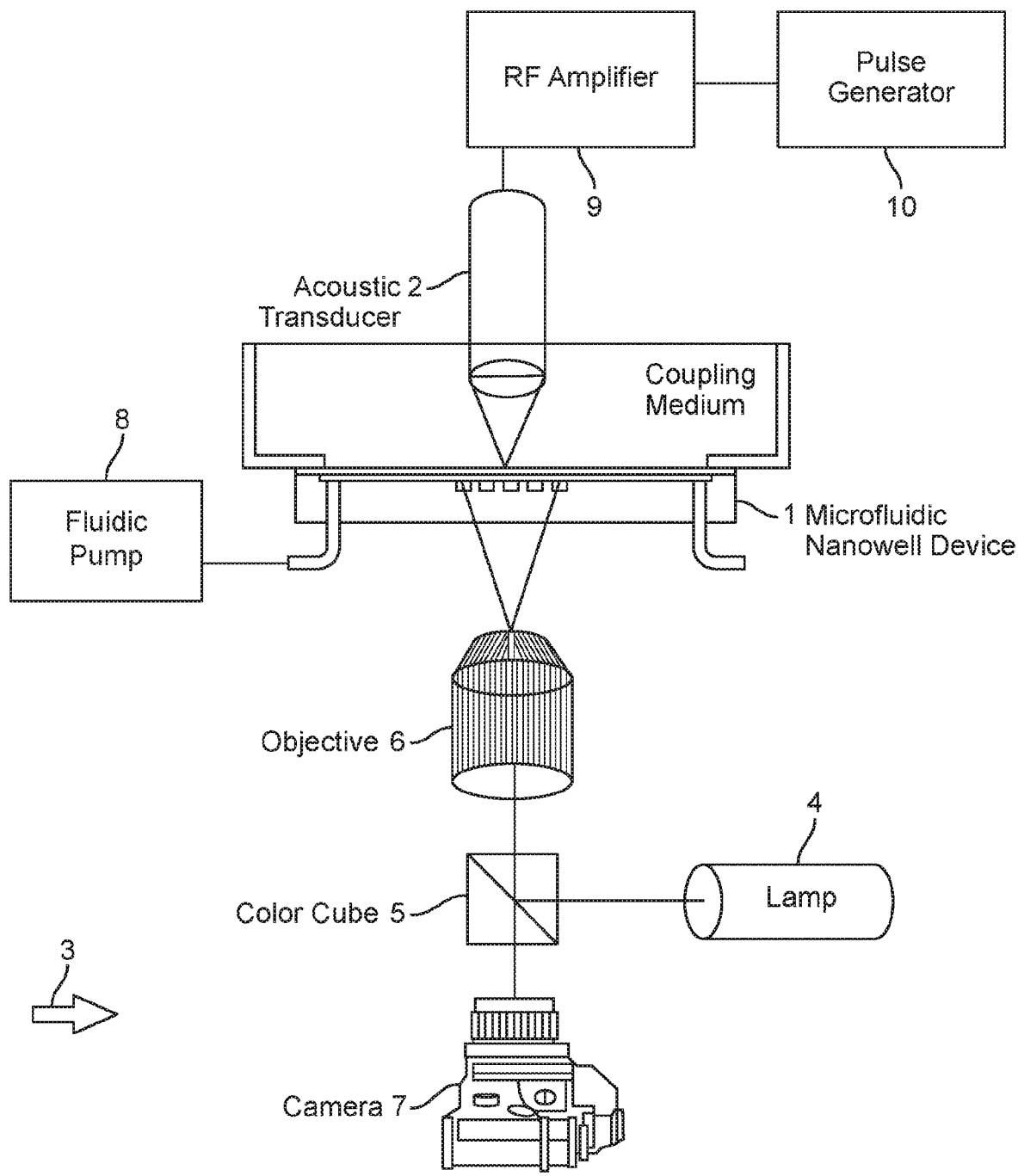
FIG. 1 shows a schematic diagram of an example platform for analysis of a large array of single cells in a microfluidic chip.

The apparatus shown schematically in FIG. 1 comprises three main parts: a microfluidic chip (1), an acoustic transducer (2), and an imaging system (3). It is advantageous to configure the apparatus of some embodiments so that the acoustic transducer and the imaging system are on opposite sides of the microfluidic chip.

Microfluidic Chip.

Figure 2:
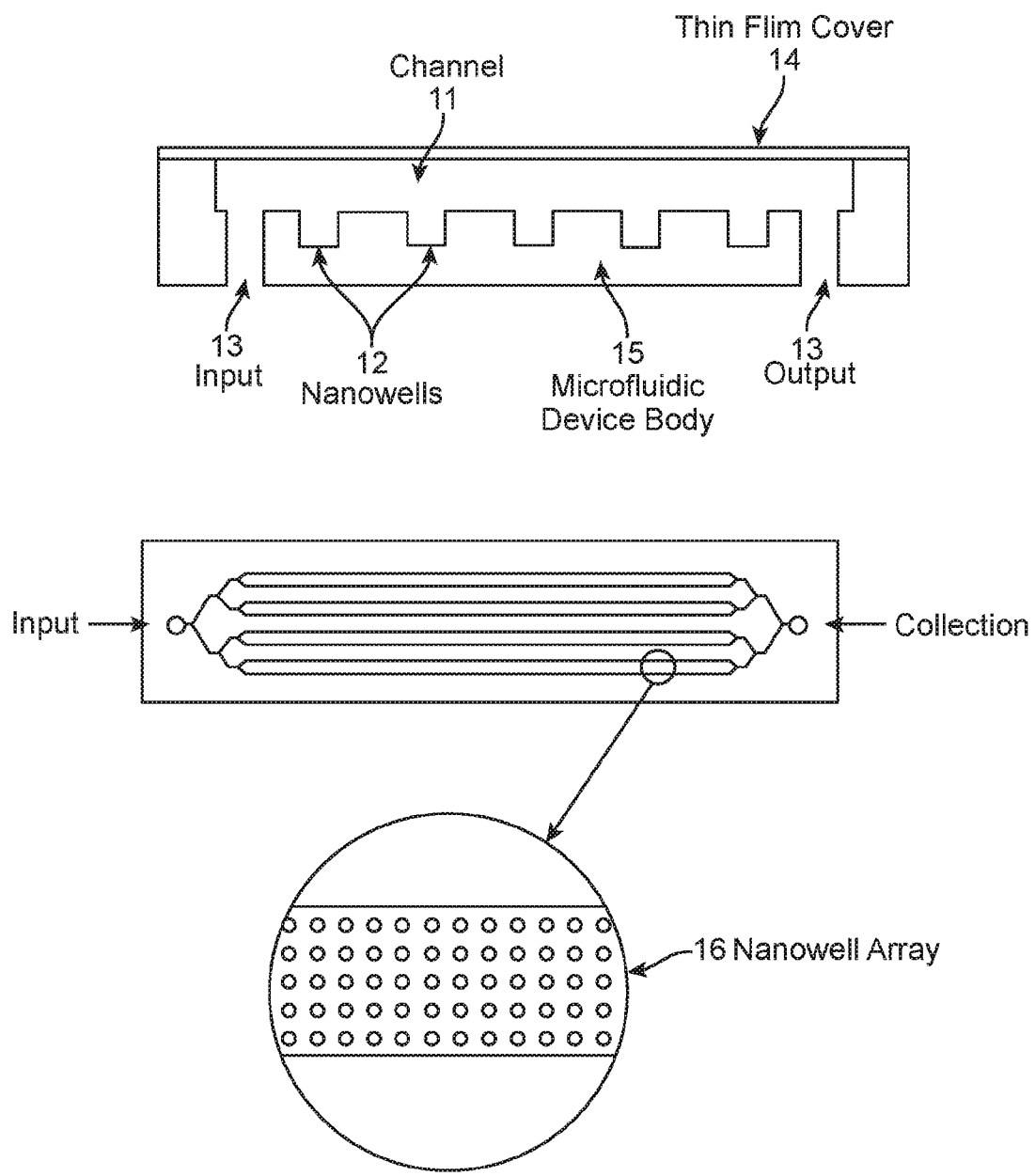
FIG. 2 shows a schematic drawing of an example microfluidic chip comprising a large array of fixed uniform volume microwells.
Figure 16:
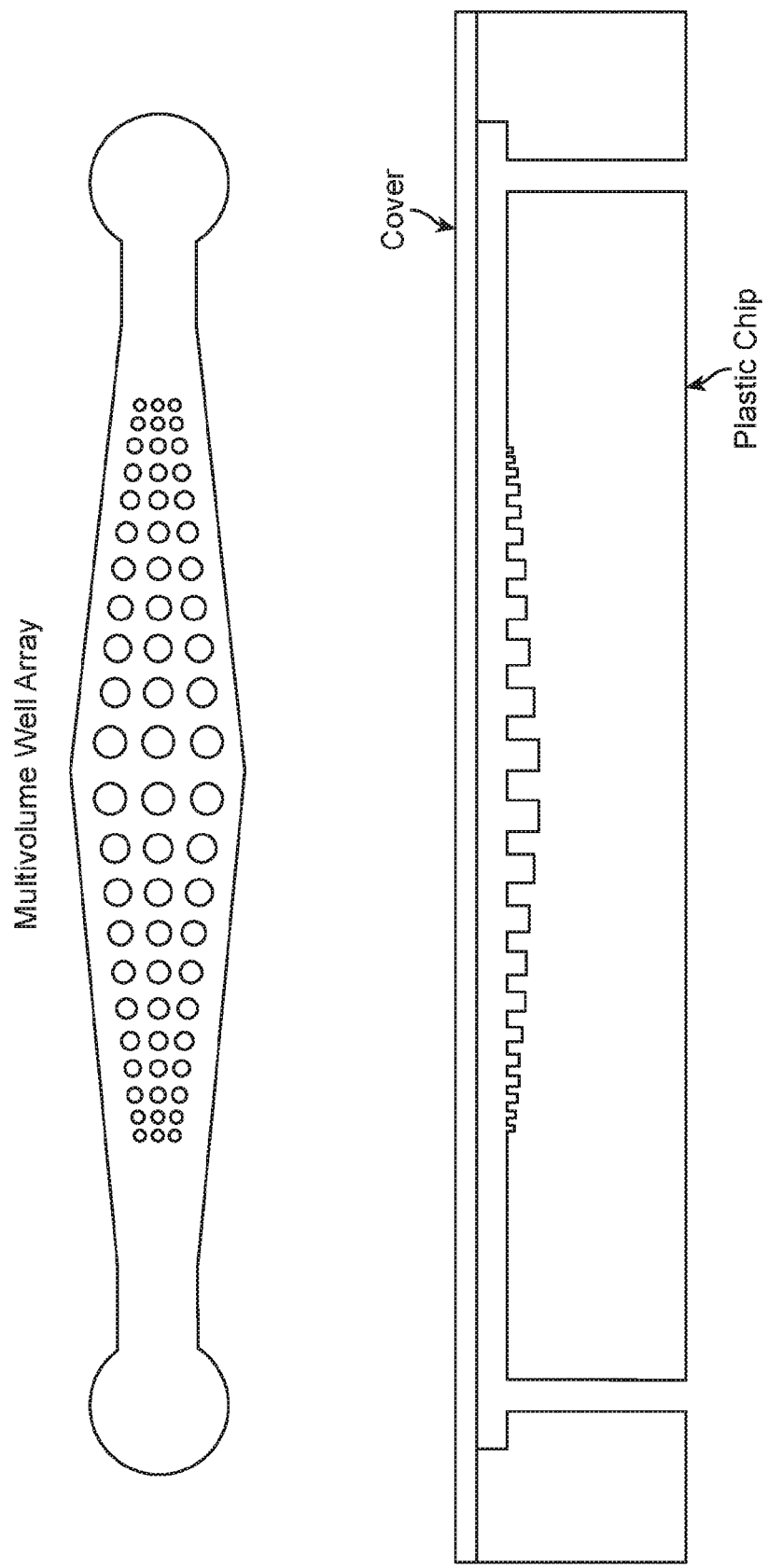
FIG. 16 shows a schematic drawing of an example microfluidic chip comprising a large array of varying volume microwells.

Two example configurations of the microfluidic chip are shown in FIG. 2 and FIG. 16. The chip can comprise an enclosed channel(s) (11) containing a dense array of microwells (12) and a network of inlet and outlet channels (13). The microwell diameter and depth can range between 10 μm-200 μm with aspect ratio ranging between 1 to 5. The dimensions of the microwells are chosen to optimize the capture of single cells of various sizes in a single well with highest probability. The well spacing can be minimized (typically in the range of 50 μm-200 μm) to increase the number of microwells within a chip such that ultra large array of single cells can be isolated within a single experiment. The format of the microwell array (16) can comprise one or more rows of wells in each channel (five rows are shown in the figure), and the device can comprise one or more channels (a four channel chip design is shown in FIG. 2 and a one channel chip design is shown in FIG. 16). The microwells can be uniform in volume as shown in FIG. 2 or varying in volume as shown in FIG. 16. The microfluidic chip can be fabricated from an optically transparent material to allow the content of the microwell to be imaged. Possible materials include polymeric substrates such as cyclic olefins (COC or COP), polymethylmethacrylate (PMMA), and polycarbonate (PC), or soft elastomers such as polydimethylsiloxane (PDMS), or glass and quartz. The channels of the microfluidic device can be sealed with a thin film (14) that is semi-transparent to an acoustic beam in the frequency range of 1-30 MHz. Possible materials include COC, COP, PMMA, PC, and polyethylene terephthalate (PET). Introduction of cell suspension, biomolecules, particles, lysing buffer, amplification reagents, wash buffers, and carrier oil into and out of the chip is controlled by an external pump (8) that interfaces with a manifold that can selectively control applied positive or vacuum pressure at specific inlet or outlet well on the chip.

Imaging System.

The compartmentalized sample in the microwells can be analyzed using an imaging system that incorporates bright field and fluorescence microscopy capabilities. A broadband light source (4) (e.g. a tungsten lamp or LED) can be filtered by a color cube (5) and illuminates the microwell array through a microscope objective (6). The magnified image of the array can be recorded using a large-format (e.g., greater than five megapixel) digital camera (7). The combination of the large format with a low magnification objective (typically 2×) provides for a large field-of-view, where typically 5000-10000 microwells can be imaged in single frame. A set of interchangeable color cubes makes it possible to measure the fluorescent signal at several different wavelengths in a sequence of images. A time sequence of images (e.g., video) can be acquired to record temporal and dynamic processes, such as the retrieval of single cells. The imaging system includes a set of interchangeable objective lenses with higher magnification (typically ranging from 4× to 60×) for high resolution imaging of single cells.

Externally Applied Acoustic Modulation.

Figure 3:
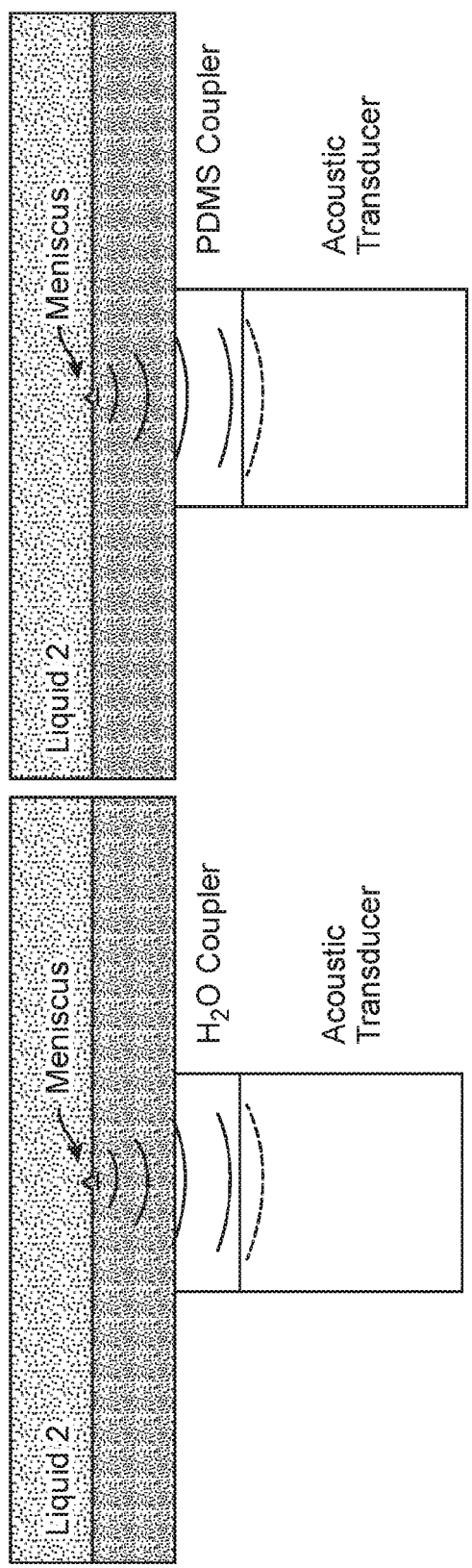
FIG. 3 shows: (A) Displacement of the meniscus at the interface of two immiscible fluids resulting from focused acoustic beam. (B) An acoustic beam is focused onto a liquid interface producing a meniscus bulge due to the pressure differential.

The retrieval of singles cells or its content within microwell compartments can be based on use of acoustic field to modulate the interface between two immiscible fluids. Modest acoustic powers can produce large displacements in the position of the interface between the two fluid phases. The basic effect is shown in the FIG. 3a, where a focused acoustic beam is used to generate a bulge in the interface between two immiscible fluids.

The acoustic transducer (2) produces a point focus at a distance of approximately 25 mm from the end of the transducer. Transducers can operate at frequencies ranging between 1 to 15 MHz, and average RF power up to 100 W. The resolution of the beam at focus increases with frequency to approximately 150 μm at 15 Mhz. The transducer is aligned to position the peak of the displacement in the center of the field-of-view of the microscope. Subsequently the position of the acoustic beam with respect to the microfluidic device can be varied by translating the microfluidic chip.

Figure 4:
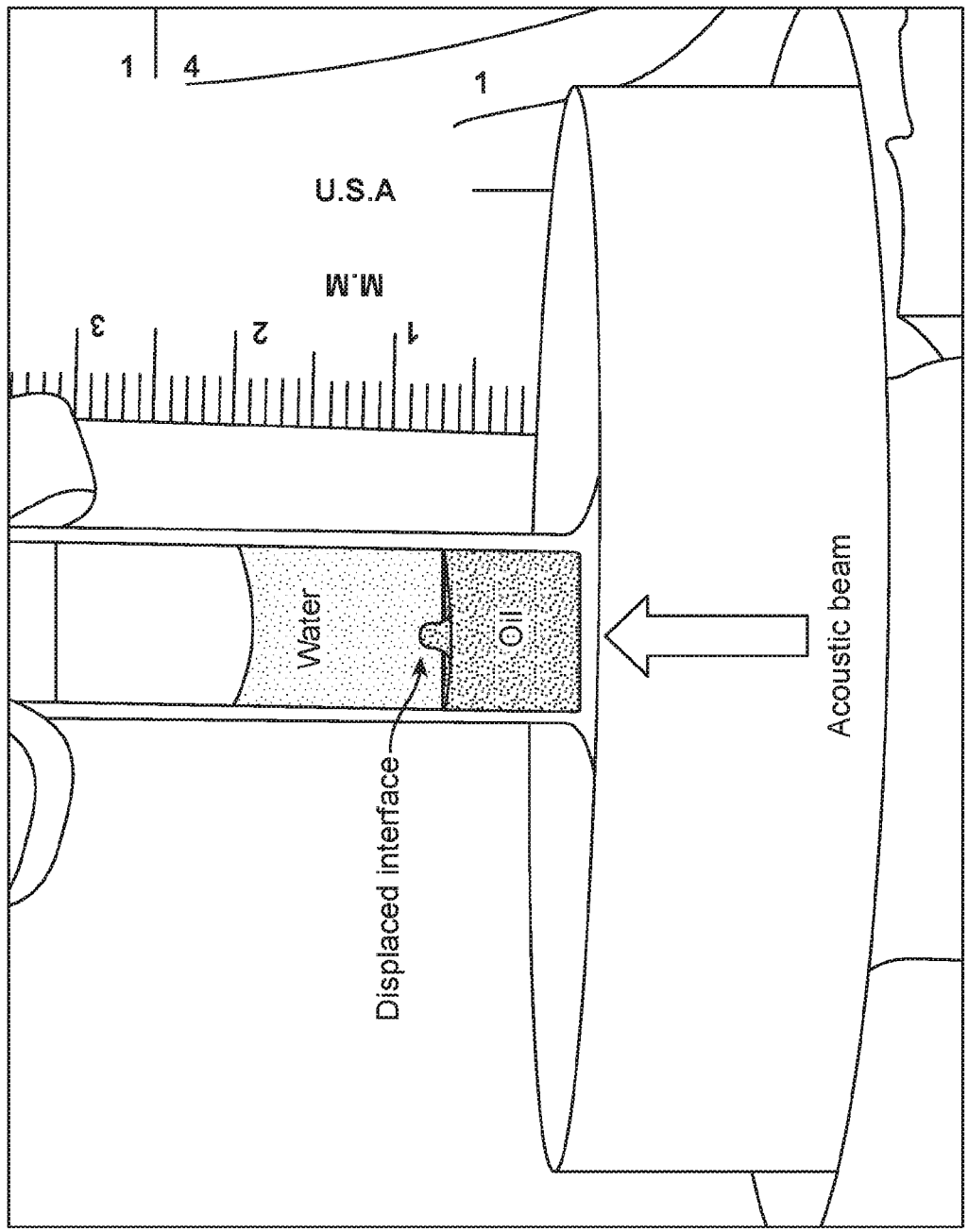
FIG. 4 shows example displacement produced by a 2.25 MHz focused acoustic beam incident at the interface of oil and water.

Initial experiments were directed at verifying the prediction that the focused acoustic beam was capable of displacing the meniscus at an oil-water interface. A 25.4 mm-diameter transducer having a focal length of 47.6 mm and operating at a frequency of 2.25 MHz was used. Several different fluorocarbon oils were investigated. An example where the oil was Novec 7500 is shown in the FIG. 4 below. A displacement of about 2 mm was obtained using an acoustic power at the transducer of 100 W.

Figure 5:
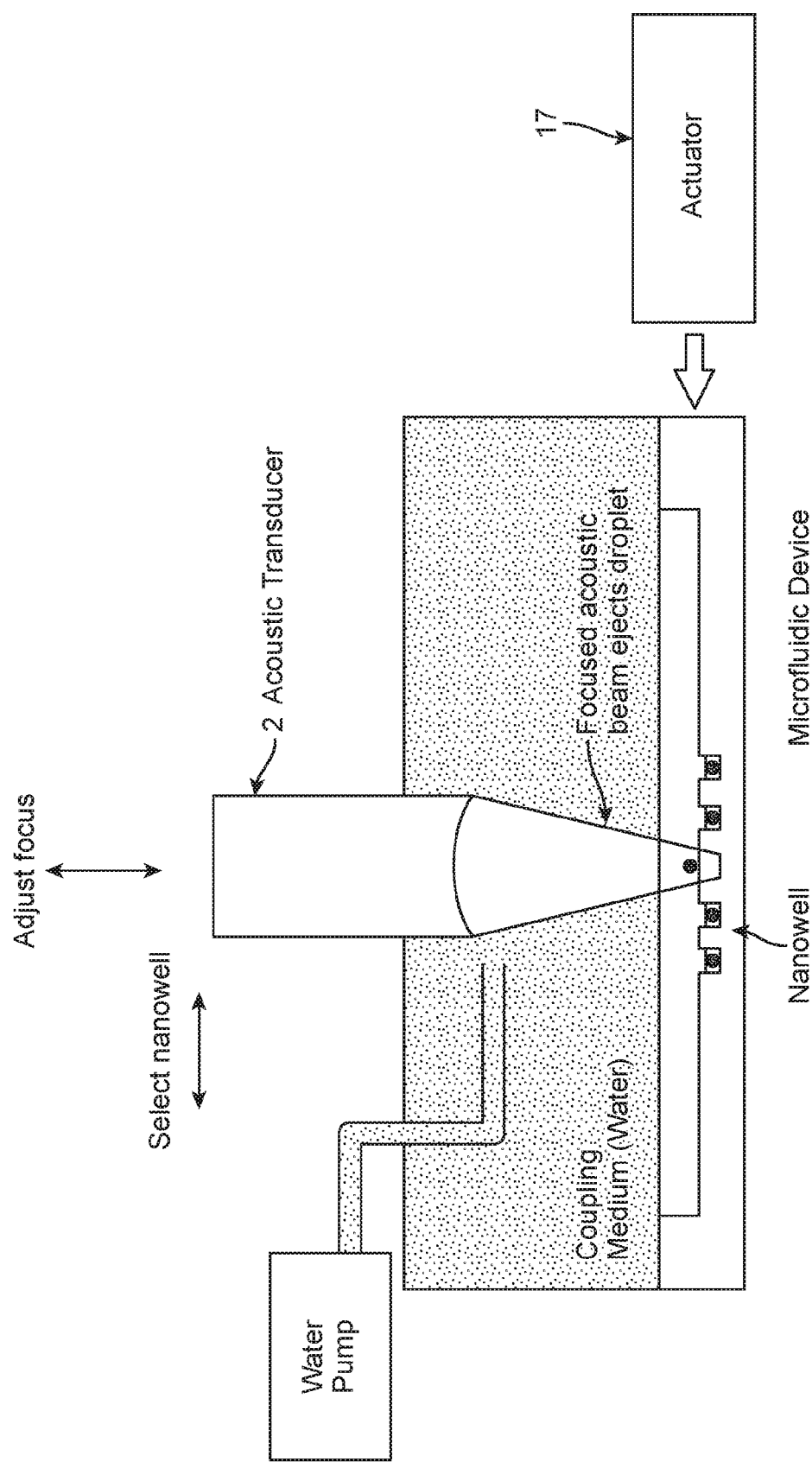
FIG. 5 shows a schematic diagram of an acoustic transducer coupled with a microfluidic chip through a water medium.

FIG. 5 shows one possible configuration of the coupling of the microfluidic chip with an externally mounted focusing acoustic transducer by immersion in a coupling medium that is acoustically transparent. Typical coupling medium include water or gel. The microfluidic device is mounted such that the thin film side is facing the acoustic transducer. The retrieval of the contents of a single microwell is achieved by positioning a high-resolution focused acoustic beam at specific microwell containing the cell of interest. The spot size of the high-resolution focus beam, ranging between 25 µm-200 µm, is achieved by operating the transducer at a high frequency and small f-number. In particular, the transducer operates in the frequency range of 1-30 MHz, with a typical value of 25 MHz. The f-number is in the range of 1-2 with a typical value of 2 (diameter=6.35 mm, focal length=12.7 mm). If water is used as the coupling medium then a water pump can be used to provide a continuous flow of water in the tank and, in particular, across the surface of the acoustic transducer to prevent trapping of air bubbles. An RF amplifier (9) providing power in the range of 1-10 W drives the acoustic transducer (2). The amplifier is modulated by a waveform generator (10) to allow operation in pulsed or continuous modes.

The acoustic beam propagates through the coupling medium and passes through the thin film cover (14) and focuses to a small spot at a position within the microfluidic channel. The microfluidic chip is translated laterally using an actuator (17) to place the acoustic beam at the position of any identified microwell in the channel. The chip is then translated vertically using the actuator (17) to adjust the width of the acoustic beam at the position of the microwell. The acoustic actuation of cells is achieved by encapsulating the microwells in a carrier phase fluid such as fluorinated oil. The acoustic beam generates a differential pressure at the interface between the carrier phase fluid in the channel and the isolated aqueous contents of the microwell. The pressure gradient generated at the interface of two fluid phases generates a localized force leading to the ejection of the microwell contents. The retrieved aqueous content containing individual cell or its lysed content is now fully encapsulated by carrier oil in the channel above the microwell arrays.

The Curvature of a Liquid Interface Meniscus Produced by a Focused Acoustic Beam.

The problem of modulating the shape of the meniscus formed between two immiscible fluids can be addressed using a focused acoustic beam propagating perpendicular to the interface. The physical configuration is shown schematically in FIG. 3*b*. The acoustic beam of power P is focused to a spot on the interface of diameter D. The acoustic field produces a pressure differential Δp across the interface. This creates a spherical bulge of radius r in the interface that we identify as a meniscus. The relationship between the pressure differential and the radius of curvature of the meniscus is given by Young-Laplace equation:

$$\Delta p = \frac{2\gamma}{r} \quad (1)$$

Here γ is the surface tension at the interface. With respect to the height h of the meniscus formed by the acoustic beam, geometry shows that, $$r = \frac{1}{2h}\left(h^2 + \frac{D^2}{4}\right) \quad (2)$$

Hence, $$\Delta p = \frac{4\gamma h}{h^2 + \frac{D^2}{4}} \quad (3)$$

Next the differential pressure produced by the acoustic beam is estimated. The pressure due to the acoustic field at any point in space is equal to the time-averaged energy density ⟨U⟩. At the interface the beam is reflected due to the discontinuity in impedance. The reflectivity R is given by, $$R = \left(\frac{Z_1 - Z_2}{Z_1 + Z_2}\right)^2 \quad (4)$$

Here $Z_1$ and $Z_2$ are the impedances of the two liquids, where we define the beam to be propagating from liquid 1 to liquid 2 as shown in FIG. 1. The values of the pressures on either side of the interface are $$p_1 = \langle U_1 \rangle = \frac{(1+R)I_0}{v_1} \quad (5)$$

$$p_2 = \langle U_2 \rangle = \frac{(1-R)I_0}{v_2}$$

The energy density can be related to the sound speed v and the acoustic intensity I according to, $$\langle U \rangle = \frac{I}{v} \quad (6)$$

Replacing the intensity by the incident power $P_0$ per unit area at the focal spot of diameter D, $$\Delta p_{12} = \frac{4P_0}{\pi D^2}\left(\frac{1+R}{v_1} - \frac{1-R}{v_2}\right) \quad (7)$$

Finally Eqs. (3) and (7) are combined to obtain an expression for the acoustic power P required to generate a height h of the meniscus at the interface:

$$P_0 = 4\pi\gamma \frac{hD^2}{(4h^2+D^2)}\left(\frac{1+R}{v_1} - \frac{1-R}{v_2}\right)^{-1} \quad (8)$$

Consider an example where liquid 1 is water and liquid 2 is the fluorocarbon oil FC-40. The material parameters for these liquids are listed in Table I. The surface tension at the interface is listed in Table II for two cases of interest corresponding to FC-40 with and without a surfactant.

TABLE I

Acoustic parameters for liquids of interest.

| Liquid | Z (MRayl) | v (m/s) |
|---|---|---|
| Water | 1.5 | 1500 |
| FC-40 | 1.86 | 640 |

TABLE II

Interface tension for liquids of interest.

| Liquid interface | γ (N/m) |
|---|---|
| Water/FC-40 | $5.2 \times 10^{-2}$ |
| Water/FC-40 + 5% EA surfactant | $2.8 \times 10^{-3}$ |

Inspection of Table I shows that the impedance mismatch between water and FC-40 is not large, and the resulting reflectivity is R=0.011. Hence there is a negligible contribution to the pressure differential at the interface from the discontinuity in the impedance. However there is a large contrast in the sound speed and it is this physical property that produces a significant pressure differential. Essentially the slowing down of the acoustic wave as it is transmitted into the FC-40 causes the energy density to increase and the pressure on that side of the interface is correspondingly higher. This causes the meniscus to bulge into the water (note that $\Delta p_{12}$ is negative when $v_2 > v_1$).

Next the acoustic power required to produce a measurable bulge in the meniscus is estimated. Assume that the focal spot has a diameter of D=200 μm and the bulge has a height of h=−50 μm (the bulge is downward), applying the values of Table I, $$P = 0.56\gamma \text{ in Watts} \qquad (9)$$

Hence for a water/FC-40 interface the acoustic power specified is 29 mW, and when the surfactant is added to the FC-40 the power specification reduces to 1.6 mW.

These power specifications correspond to the acoustic power incident on the interface. In an application there will typically be significant losses of power between the transducer and the interface. For example, assume there is a layer of PDMS of thickness T=5 mm that the acoustic beam traverses to reach the interface. The acoustic attenuation coefficient in PDMS at a frequency of 10 MHz is approximately α=50 dB/cm. Using the relationship $$\frac{P_0}{P} = 10^{\left(\frac{\alpha T}{10}\right)}, \qquad (10)$$

it is found that in this case the power $P_0$ at the transducer is reduced by a factor of 316 due to the attenuation in the PDMS. Hence a transducer power of 9.2 W in the case of no surfactant is specified, and 0.5 W in the case where the FC-40 contains the surfactant.

Workflow.

Figure 6:
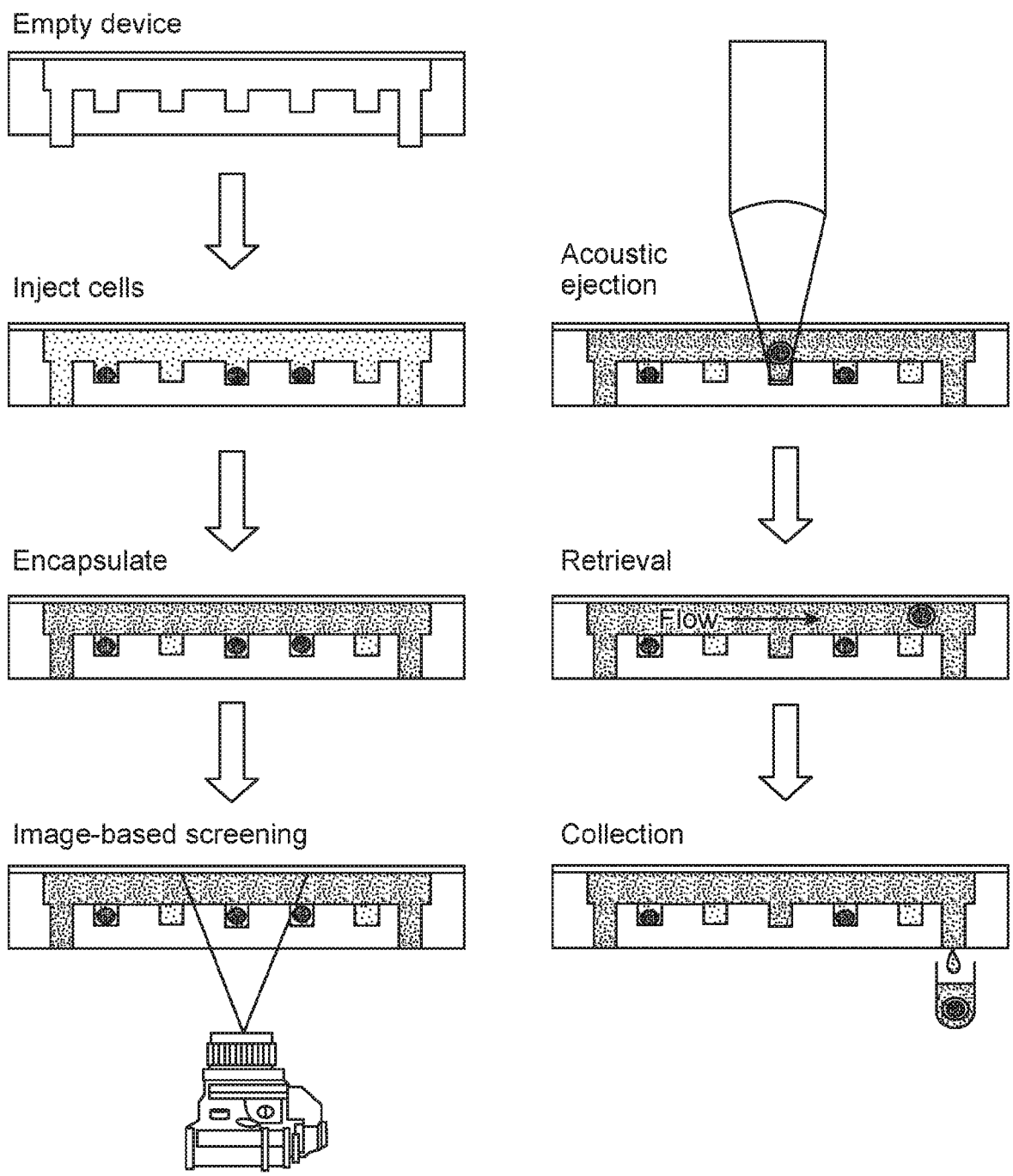
FIG. 6 shows a schematic diagram of an example workflow steps for single cell isolation, screening, and retrieval.

An example workflow of cell suspension loading, isolation, imaging, and retrieval is depicted schematically in the FIG. 6. Cell suspension of optimized density is introduced into the microfluidic chip by flow and isolated individually in the microwells. One method of introducing the cell suspension is to apply vacuum pressure for a few minutes to remove trapped air in microwells followed by exposure to atmospheric pressure to flow the suspension into the evacuated chip in order to rapidly fill the microwells with single Cells. A second method is to apply pressure to flow the suspension over the microwell arrays and allow the cells to settle into the microwells over a period of time. Both methods can result in single cell capture efficiencies in the range of 25% to 60% based on optimization of microwell geometry and cell suspension density. The cells remaining outside of the microwells can be removed by flowing wash buffer solution.

The isolated cells can then be screened by imaging under bright field and fluorescence microscopy. Since the trapped cells are now spatially indexed, they can also be imaged at different magnification, optical wavelengths, temperature, and time. The fluorescence imaging can be used to screen the isolated single cells for specific events such as a genetic reporter within the cell or protein marker on the cell surface or secreted proteins.

Figure 7A:
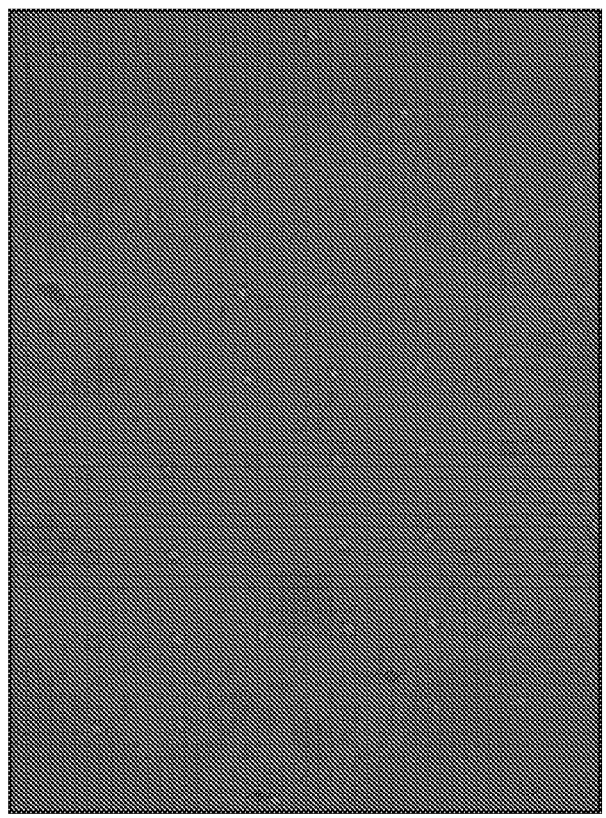
FIG. 7 shows images of isolated GFP expressing single cells in an array of 50 μm diameter microwell array. The filling efficiencies of single cells for sample a and b are 61.7% and 50%, respectively.
Figure 7B:
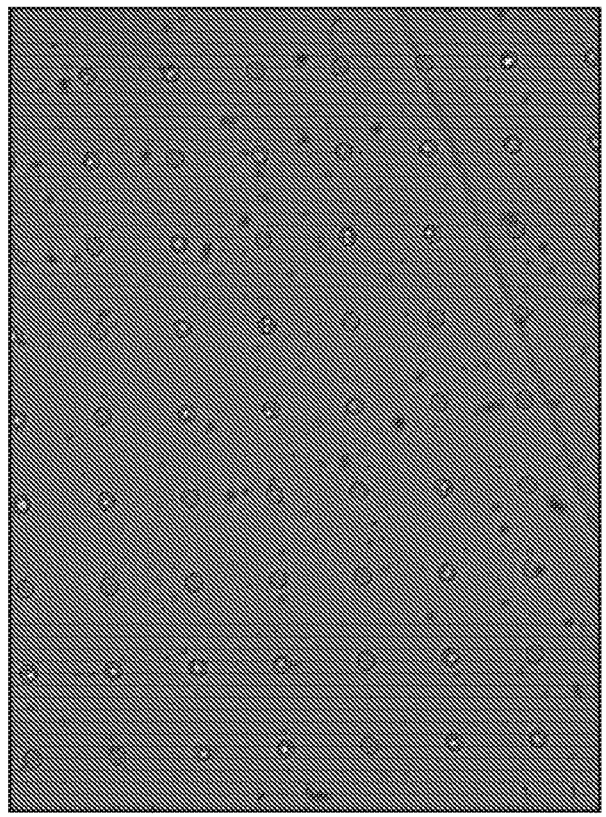

FIG. 7 illustrates two examples of high magnification images of GFP expressing U87 cells isolated in 50 μm diameter microwells. The cells remaining outside of the microwells were removed by flushing with 1×PBS. The isolated cells were subsequently encapsulated by flowing into the chip a fluorinated oil. The density of cell suspension solution prior to loading was approximately $1.0 \times 10^6$ cells/ml. In FIG. 7a there are a total of 68 observable microwells with 42 containing single cells resulting in a filling efficiency of 61.7%. A single microwell within the image is observed to have 2 cells. In FIG. 7b, there are 32 microwells that contain single cells resulting in filling efficiency of 50%. There are also 3 microwells that contain two cells. The strongly GFP expressing cells and be identified and subsequently retrieved for clonal expansion.

Figure 8:
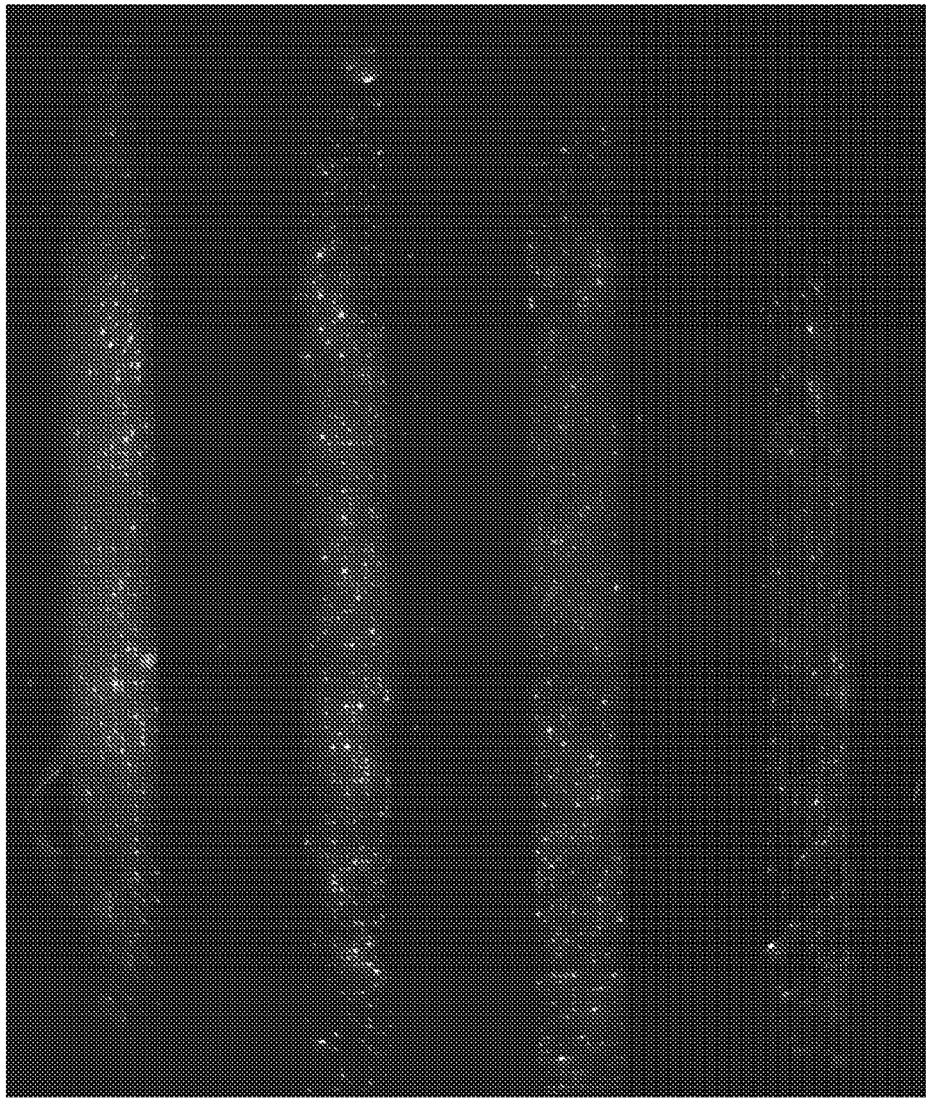
FIG. 8 shows a large area image of an array of U87 single cells isolated in microfluidic chip (see FIG. 2) containing 4 channels each containing about 5000 microwells. The cells were pre-labeled with FDA live cell staining prior to introducing into the chip.

The correlation of multiple fluorescent probes can be used to perform complex screening techniques. The image-based data collection provides high throughput by making measurements on large number of cells simultaneously. FIG. 8 shows large array imaging of isolated single U87 cells in the microfluidic chip design shown in FIG. 2. The cell suspension were pre-labeled with live cell stain fluorescein diacetate (FDA) and then introduced into the chip by vacuum fill. The screening process generates information about the statistical distribution of characteristics of the ensemble of single cells. This information is valuable in its own right, but it also allows the unique cells that correspond to the outliers of the distribution to be identified.

Figure 9A:
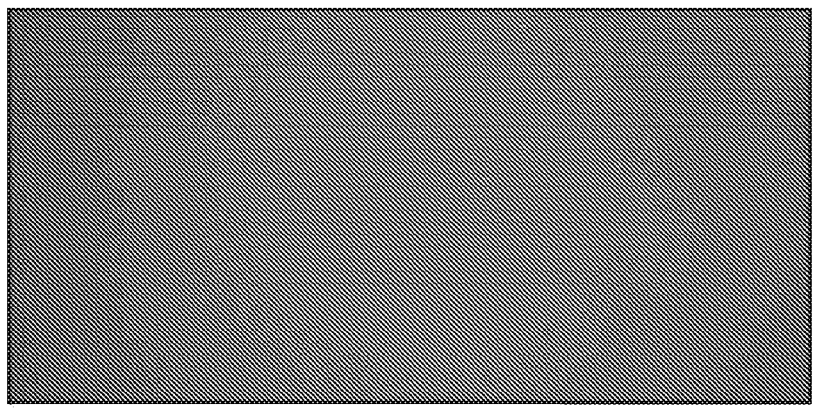
FIG. 9 shows (a-c) images of on-chip live cell staining of isolated single U87 cells, depicting rapid staining of the cells resulting from flow of FDA solution over the array of microwells
Figure 9B:
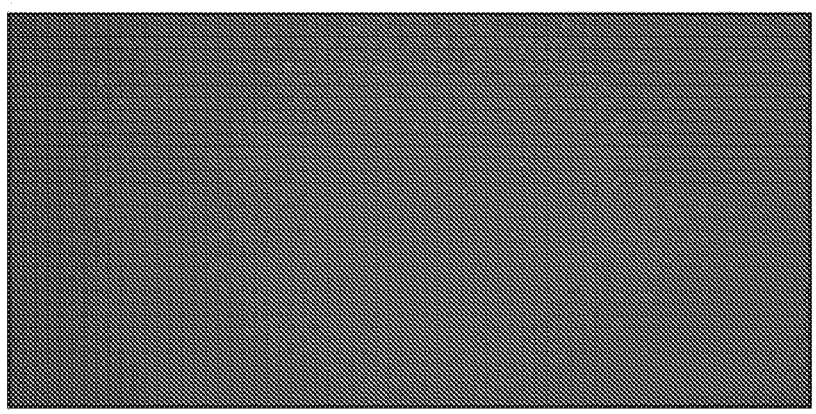
Figure 9C:
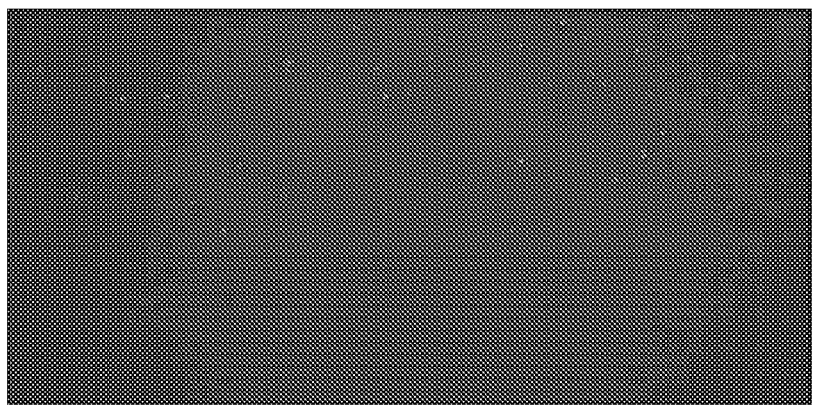
Figure 10A:
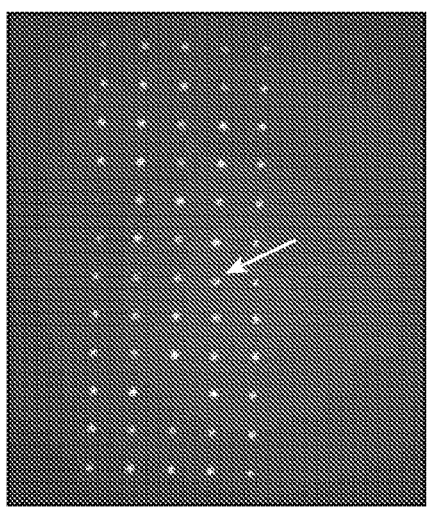
FIG. 10 shows the ejection and retrieval of single cell within a microwell with use of acoustic focused beam. Sulfur Rhodamine 101 was added to the microwells after isolation of the cells in order to better visualize the microwells. (a) The acoustic beam is positioned on the single microwell of interest containing the single GFP expressing U87 cell. (b) The acoustic beam is applied in short pulses resulting in initial distortion of the microwell content. (c) The single cell is now ejected and encapsulated within a droplet. (d) through (f) show the droplet containing single cell flowing downstream where it can be collected for further processing.
Figure 10B:
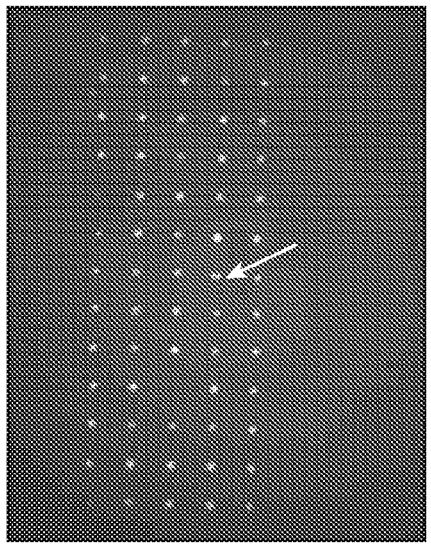
Figure 10C:
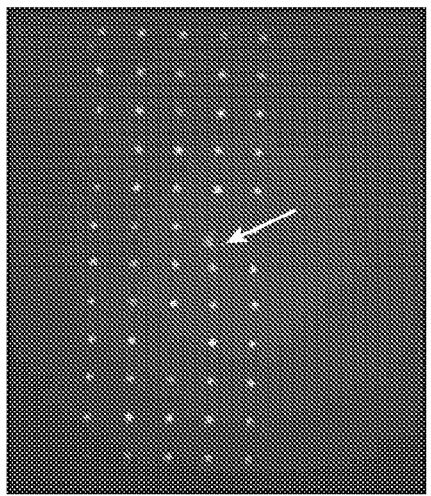
Figure 10D:
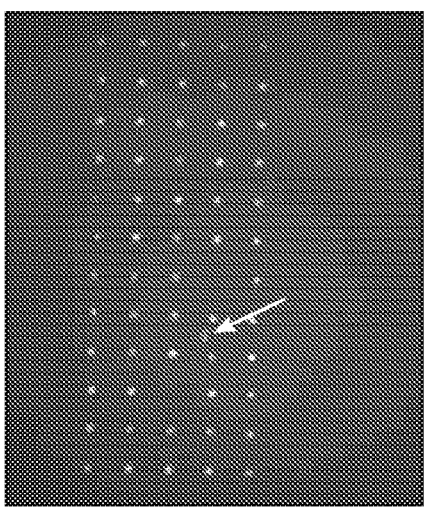
Figure 10E:
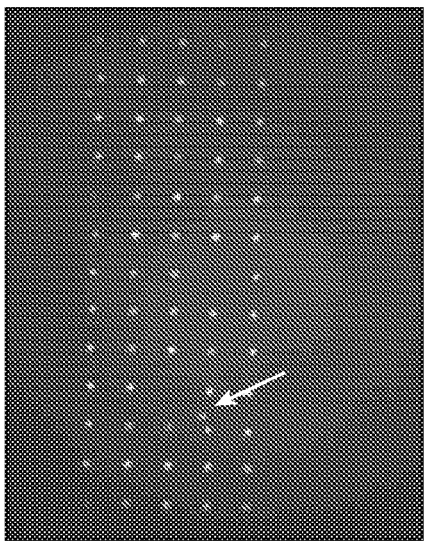
Figure 10F:
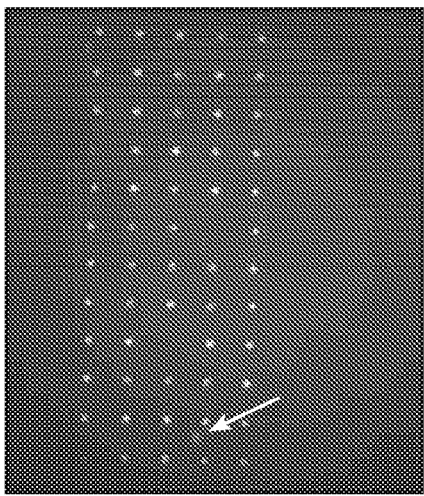

After the cells are isolated within the microwell arrays, additional reagents (e.g. lysis buffer, functionalized beads with capture antibodies or barcodes, amplification reagents, wash buffer) can be introduced into the chip and allowed to mix with the trapped cells by diffusion or settling in case of beads. The last fluid to be added is the carrier oil, typically fluorinated oil, which isolates the trapped cells from adjacent microwells and prevents evaporation. It is preferred that the carrier oil has a very low solubility of water (<10 ppm) making the device stable for long periods (>1 h). To demonstrate capability of adding reagents sequentially, on chip staining and lysing of isolated single cells are performed. The embedded movie shown in FIG. 9 illustrates on-chip FDA staining of the trapped GFP expressing U87 cells within microwells. The isolated cells are rapidly stained with the introduction of the FDA. The stained cells were subsequently lysed (data not shown) with introduction of lysis buffer where the FDA stain was observed to wash away. The ability to add reagents sequentially allows a number of applications where the isolated cells can be lysed and the genomic content amplified and retrieved for next-generation sequencing. Applications include RNA-sequencing and whole genome sequencing.

The single cells of interest or its content can be retrieved from the microwells on demand and collected for downstream processing such as next-generation sequencing. The series of images in FIG. 10 illustrate the retrieval of single GFP expressing U87 cell from a microwell. Sulfur rhodamine 101 dye was added to the microwells by flow after cell isolation step in order to visualize their exact location. The retrieval process allows the microwell array to be covered with the carrier oil phase. Retrieval of a single cell is achieved by applying an extrinsic generated focused acoustic beam as described earlier. To retrieve the cell of interest the focal spot of the acoustic beam is positioned in close vicinity of the microwell location. The acoustic beam is then applied in a burst of short pulses, typically numbering 5-20 and having a period of 10-100 ms, in order to generate radiation pressure force at the water-oil interface. The pressure forces at the interface drive the oil phase into the microwell resulting in the entire content to emerge from the well as a single aqueous droplet. The trajectory of the ejected droplet can be controlled by the relative position of the acoustic beam with respect to the microwell. When using higher density oil, the buoyancy of the aqueous droplet prevents the ejected droplet from being recaptured in an empty microwell. Once ejected within the flowing carrier oil, the droplet can be collected downstream within a larger well or in microtiter plate outside the chip for further processing.

The retrieval process promote ease of ejection and unimpeded flow of aqueous droplets in the oil phase. Surfactants can be added to the fluorocarbon oil to suppress the interaction of the ejected aqueous droplet with aqueous content in nearby microwells and the surface of the channel. Also dynamic or permanent surface coating can be applied to the microfluidic chip prior or during aqueous filling in order to reduce the interface energy, and thereby facilitate the droplet ejection and prevent aqueous wetting.

Use of Acoustic Beam Forces for Valving and Sorting.

Figure 11A:
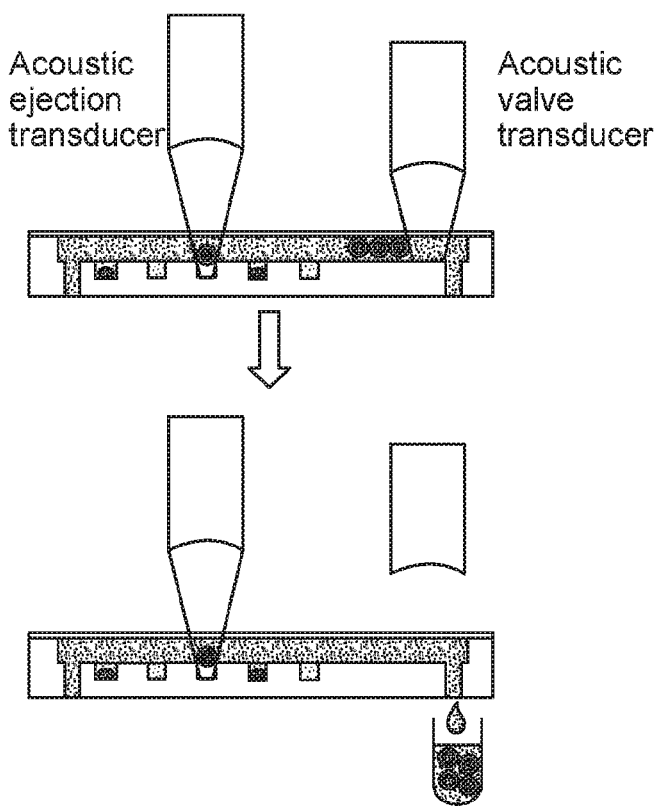
FIG. 11 shows: (a) Schematic diagram depicting a mode of operation for acoustic valving. (b) Series of images from captured video illustrating the acoustic valving capability. In the on mode, the acoustic valve prevents the flow of the ejected droplets past the converging channel. The last image shows the droplets being swept out by flow when the defocused acoustic beam is no longer applied.
Figure 11B:
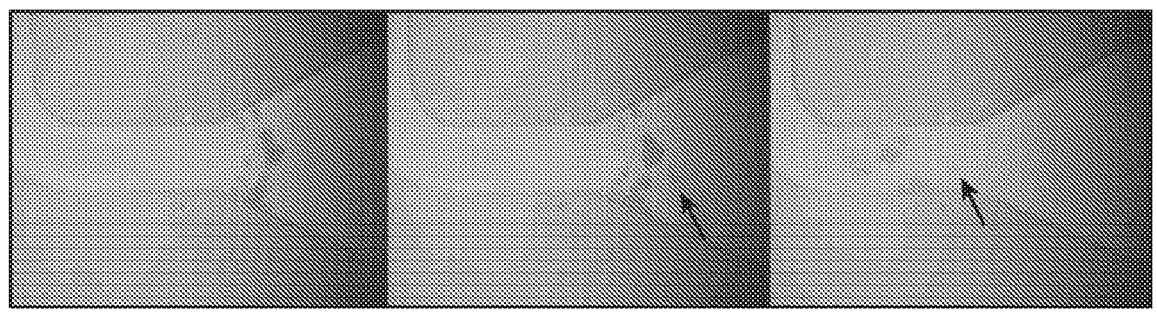

Aqueous droplets containing single cells can also be manipulated in the microfluidic device using a second acoustic transducer. In one embodiment a defocused acoustic beam can trap droplets and hold them against a modest flow, as shown in the FIG. 11a. In this example there are two acoustic transducers: one is used to retrieve the contents of microwell, the other to block the flow of generated droplets such that they are collect in an outlet channel. Note that the flow of the oil phase is not impeded by actuation of the second the acoustic beam; the acoustic beam acts as a valve for only the droplets. The series of images in FIG. 11b show experimental data on the ability to prevent flow of ejected droplets from exiting the chip by applying defocused acoustic beam. In the first image the droplets are held in place by the acoustic forces. In the second image a single droplet from upstream is approaching the valving region. In the last image the acoustic beam is turned off and the droplets are swept out by flow.

Figure 12:
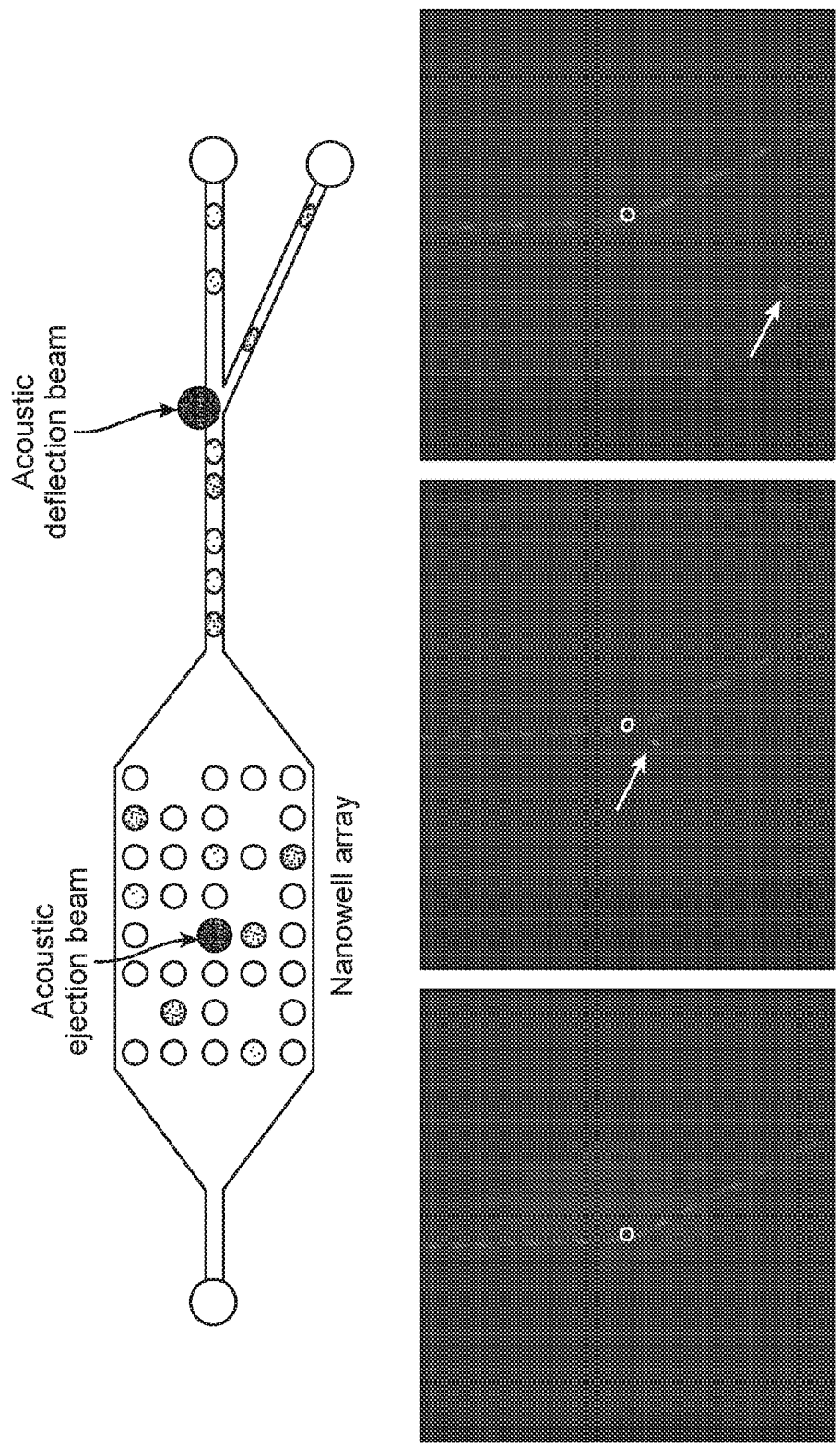
FIG. 12 shows use of an external defocused acoustic beam to sort individual droplets. The series of images illustrates the sorting of single fluorescence droplet in a microfluidic chip.

Another embodiment of an acoustic actuator is to use a defocused acoustic beam to deflect droplets at a channel junction as shown in FIG. 12. In this example one acoustic transducer is used to retrieve droplets from the microwells, and the other transducer is used to deflect specific droplets at the junction to perform a sorting operation. In this mode the acoustic beam can be used to sort the retrieved cells and route them in a network of collection channels.

Applications.

Within large pharmaceutical companies flow cytometry is an established tool for use in protein detection in single cells; however, the cell viability is of major concern. There continues to be a need for high throughput technologies for screening at the single cell level (for example screening of hybridoma, antigen-specific B-Cells and T-Cells) for antibody discovery and retrieval for clonal expansion. Other key applications within the pharmaceutical industry include cellular response at the single cell level to drug targets and antibody repertoire sequencing of genomic DNA and mRNA.

Single cell genome and transcriptome sequencing of genomic content is now being widely used for genotyping as indicated by large number of research publications and few number of startup companies. Clinical applications and cancer diagnostic include the screening for rare cells, for example circulating tumor cells (CTCs), in an enriched sample.

The platform described herein can be applied to analyze ultra large array of single cells for the applications listed above. The platform described herein includes an automated high throughput integrated system that performs isolation of single cells, reagent addition, image-based screening, and retrieval for follow-on analysis such as sequencing.

Additional Advantages.

Additional advantages of some embodiments of the methods and devices described herein include the following:

An automated high throughput platform that can isolate ultra large number of single cells in microwells having volume ranging between about 10-100 picoliters to several nanoliters.

The microwell array permits compatibility with cells of various sizes.

Reagents such as lysis buffer, functionalized beads for barcoding or protein capture or combinatorial library studies, and other buffers can be added sequentially.

Miniaturization can lower reagent consumption and subsequently lower the cost

Spatial location of each trapped cell is registered within the microfluidic chip permitting temporal studies.

Multicolor imaged based screening based on fluorescent marker can be conducted on the isolated cells rapidly, approximately 5000 to 10000 microwells can be imaged in single frame at low magnification.

Carrier oil flow encapsulating the microwells isolates the trapped single cells and minimizes evaporation during experimental study or heat treatment.

A focused acoustic beam generated by transducer outside the chip is used for automated retrieval of contents within the microwells and also compatible with fragile cells.

The retrieval method does not require fabrication of internal components for the microfluidic chip thus greatly simplifying manufacturing process to those commonly used today such as, though not limited to, injection molding or hot embossing.

Enclosed system to prevent extrinsic contamination sources.

Existing platforms are capable of processing at most 100 cells and may require upstream cell sorters that are very expensive and may alter the genomic content or decrease cell viability. In some embodiments, the methods and devices described herein integrate and automate the isolation, screening, and retrieval of thousands of single cells within a single experiment.

Additional Features.

Additional features of some embodiments of the methods and devices described herein include the following:

- An integrated platform that is automated for isolation, analysis, and retrieval of single cells or its content.
- An extrinsic generated focused acoustic beam for retrieval and manipulation of single cells or contents of microwells.
- Enclosed system for rapidly isolating single cells in microwell array by vacuum fill. The enclosed environment is also beneficial in minimizing sources of contamination.
- Capability to add reagents sequentially to the trapped single cells in a closed system by flow.
- Ability to conduct temporal studies on isolated single cells with on-chip registry.
- Isolation of the trapped single cells by flow of an immiscible fluid (for example fluorinated oil) that isolates the contents within the microwells. The oil also minimizes evaporation of the aqueous content during temporal studies that may take hours.
- An optional modification includes the addition of heating capability within the system to conduct amplification of the genomic content within the microwells. This may involve rapid heating and cooling capability to reach temperatures of 95° C.

Additional Embodiments

Additional embodiments include a microfluidic device containing two (or more) immiscible fluids that are in contact at an interface. An acoustic field, generated by an external transducer, can be applied to the region surrounding the interface. A differential pressure can be induced at the interface due to the difference in acoustic energy density in the two fluids. The pressure can result in a force that can be used to modulate the position of the interface. The modulation of the interface can be restricted to a localized region by using a focused acoustic beam, and can be modulated in time by gating the acoustic beam.

Additional Embodiments

Multiplex Digital PCR with capability to select and retrieve positive reaction microwells for target enrichment and downstream processing. Features of this embodiment include the following:

- Platform capable of digital quantitative real-time PCR.
- Microwell arrays of uniform or varying volume.
- Use of multiple fluorescent probe colors and melt-curve analysis in order to achieve high level of multiplexing.
- Retrieval of allele specific amplified targets for enrichment of genetic content for downstream sequencing.
- Rapid thermocycling due to close contact of microfluidic substrate with heating elements.
- Rapid analysis of microwell array due to image-based readout.

WORKING EXAMPLES

Example 1—Digital PCR

Figure 13:
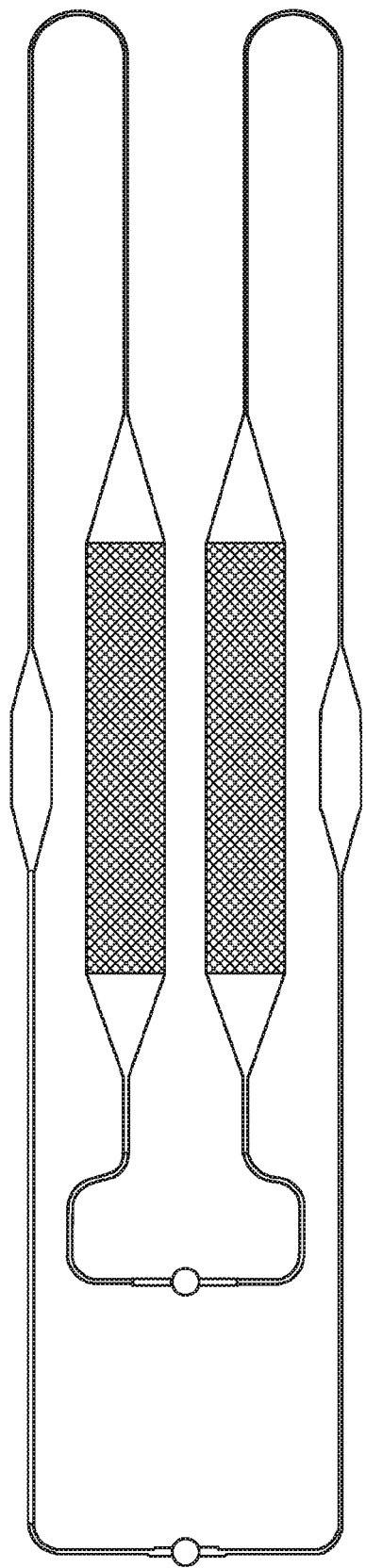
FIG. 13 shows a sample polydimethylsiloxane (PDMS) microfluidic chip design for digital PCR containing a large array of uniform volume microwells.

A sample polydimethylsiloxane (PDMS) microfluidic chip design for digital PCR containing large array of microwells is shown in FIG. 13. The chip contains a total of 8350 microwells divided between two individual tracks. The 90-picoliter microwells have dimensions of 50 μm in diameter and depth.

The chip was vacuum filled with premixed nucleic acid and TaqMan probe PCR master mix. The system is flexible enough to allow use of other amplification reagents. The microwells were partitioned by flushing the chip with fluorinated oil that seals the individual microwell and prevents evaporation. FC-40 oil was chosen as the fluorinated oil. PDMS is a porous substrate and rapid evaporation of aqueous phase occurs at high temperatures. To minimize the evaporation, a second water flow-cell chip was plasma bonded to the topside of the device and flushed with water during thermocycling. The issue with evaporation through the porous substrate would be eliminated with use of plastic substrates such as Cyclic Olefin Polymers.

The chip was next placed on a flatbed block thermocycler (MJ Research PTC 200) and clamped down in place to maintain good thermal contact with the copper plate placed on top of the block. Glycerol was added between the block and copper plate to provide good thermal contact.

A single color optical system was setup above the thermocycler that is capable of imaging 100s of microwells during each PCR cycle in order to monitor and record time-lapse images of the amplification. This imaging capability during thermocycling allows the ability to generate PCR curves from each individual microwell, similar to qPCR instruments thus becoming a digital qPCR.

Figure 14:
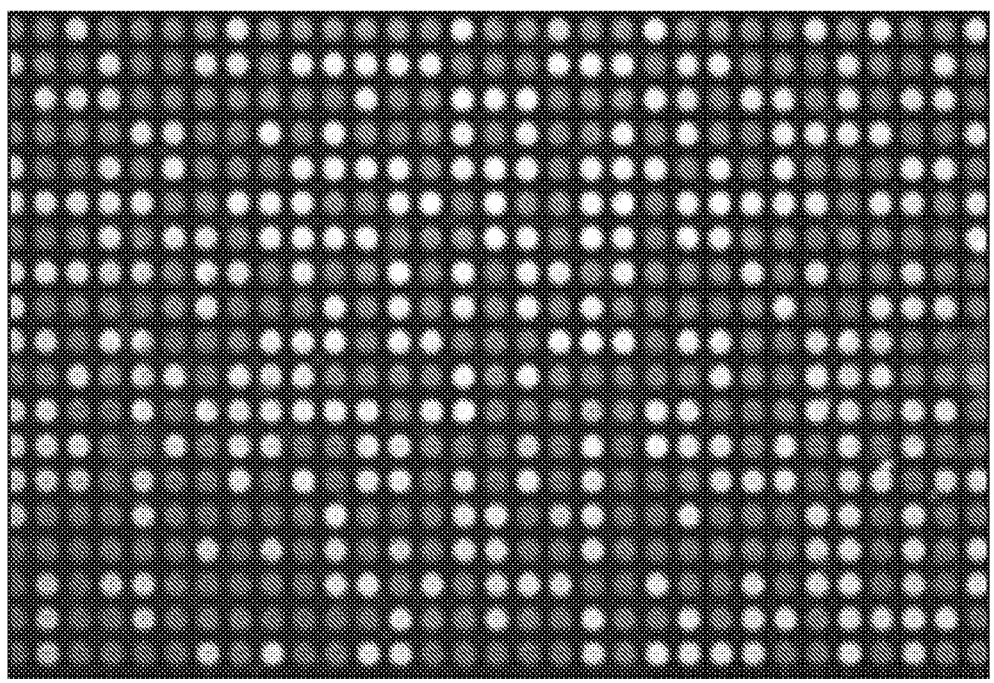
FIG. 14 shows an expanded view of 589 microwells post amplification (40 cycles). The detection of the target template is shown in the high fluorescence signals from the microwell that indicate 46.6% positive microwells. Using Poisson distribution calculation one can determine the starting concentration of the DNA sample.
Figure 15A:
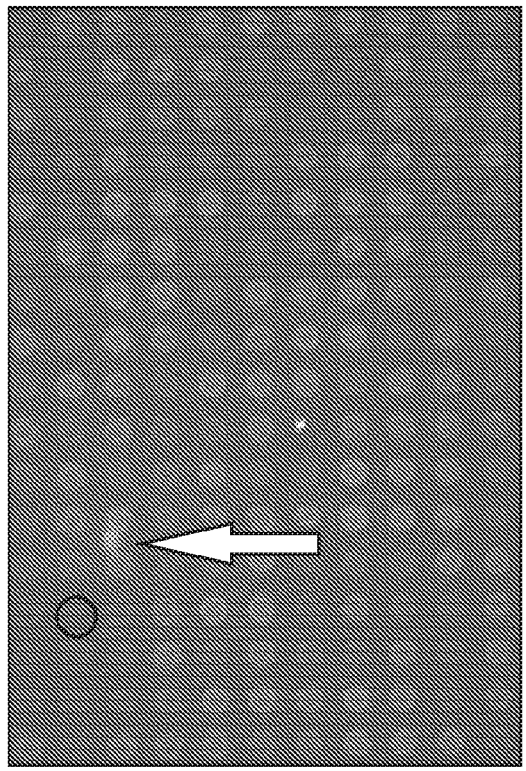
FIG. 15 shows the ejection of the positive microwell into a flowing stream of fluorinated oil containing surfactants generating a droplet that can be collected for further analysis.
Figure 15B:
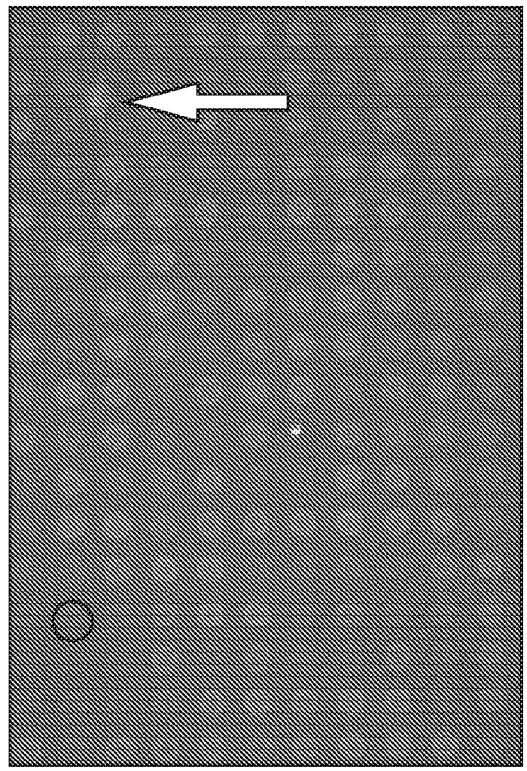
Figure 15C:
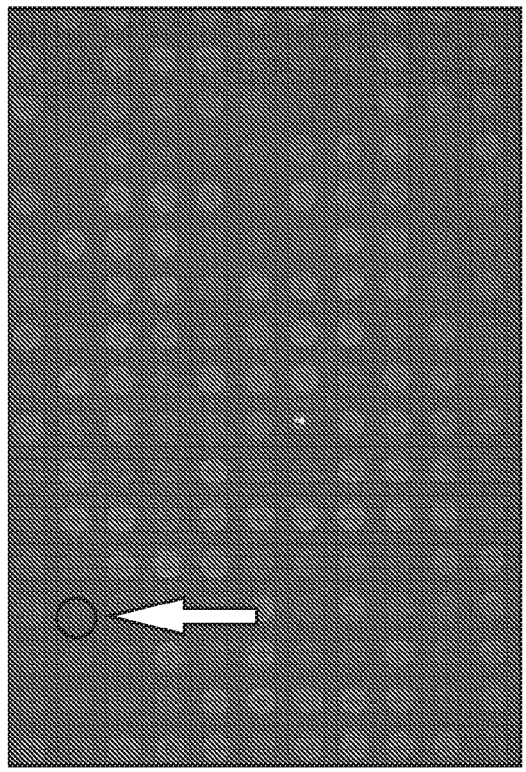
Figure 15D:
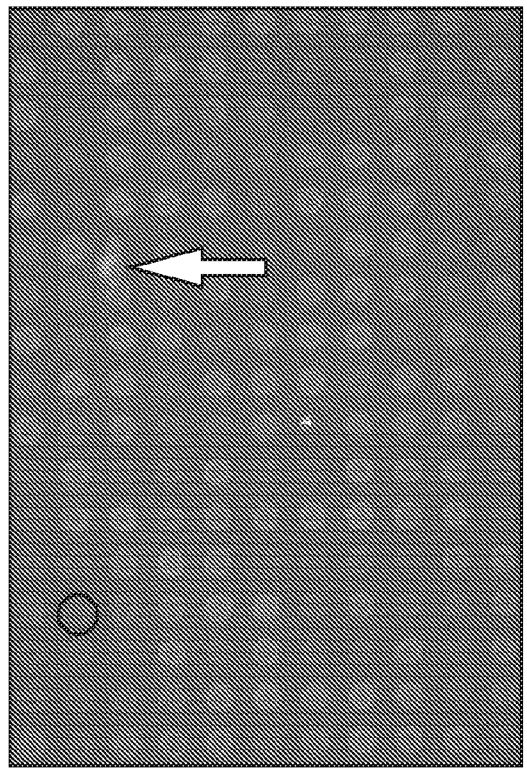

FIG. 14 is an expanded view of 589 microwells post amplification (40 cycles). The detection of the target template is shown in the high fluorescence signals from the microwell that indicate 46.6% positive microwells. Using Poisson distribution calculation one can determine the starting concentration of the DNA sample.

This platform has the capability to retrieve the contents of the positive wells, using an extrinsic acoustic mechanism, for downstream processing such as next generation sequencing. FIG. 15 demonstrates the ejection of the positive microwell into a flowing stream of fluorinated oil containing surfactants generating a droplet that can be collected for further analysis.

The experiment described above demonstrates the capability of an integrated digital platform where the sample input analyte can include not only single-cells, but also nucleic acids, proteins, other biomolecules, and organic and inorganic particles.

Example 2—Simulation of the Performance of a Multivolume dPCR

Multivolume array can be used for digital PCR. Present here are simulations of the performance of one embodiment of this chip, which is compared to the results to a chip having an array of uniform volume wells. The arrays chosen have nominally similar sensitivity and dynamic range. This means that the arrays are able to measure the concentration of the target over the same range, and hence their performance can be directly compared.

The uniform array is characterized by the number of wells N and their diameter $d_0$. The depth of the well is equal to the diameter (an Enplas design rule) so that the volume of the well is:

$$V_0 = \frac{\pi}{4} d_0^3 \qquad (11)$$

The total volume of the array is:

$$V_{TOT} = \frac{\pi}{4}d_0^3 N \quad (12)$$

The separation of the wells is equal to the depth (same Enplas design rule). Assuming the wells are close-packed hexagonal array to conserve space, the total area of the array is:

$$A_{TOT} = \frac{4N}{\sqrt{2}}d_0^2 \quad (13)$$

The geometry of the multivolume array is more complicated. The general design is shown in FIG. 16. The diameter of the wells increases linearly from the ends of the channel towards the center such that:

$$d_n = d_0 + n\delta, \; n=0,\ldots,N \quad (14)$$

Here $d_0$ is the diameter of the smallest well, $d_N$ is the diameter of the largest well, and there are 2(N+1) wells in each row. The parameter $\delta$ is the incremental increase in the well diameter. There are M identical rows across the width of the channel. Hence the total volume of the array (assuming 1:1 aspect ratio) is:

$$V_{TOT} = 2M \sum_{n=0}^{N} \frac{\pi}{4} d_n^3 \quad (15)$$
$$= \frac{\pi M(N+1)}{8}[d_0^3 + 6d_0^2 \delta N + 2d_0 \delta^2 N(2N+1) + \delta^3 N^2(N+1)]$$

If the spacing of the wells is equal to their depth (i.e. diameter) then the total area of the multivolume array is:

$$A_{TOT} = M(2d_0 + \delta N)[4d_0 + 2\delta N(N+1)] \quad (16)$$

The designs of the uniform and multivolume arrays used in these simulations are matched, in the sense that they have the same sensitivity and dynamic range. The sensitivity (minimum detectable concentration) is simply related to the total volume of the wells:

$$C_{min} = \frac{10}{V_{TOT}} \quad (17)$$

This is true for both the uniform and multivolume arrays. Previously a different version of Eq. (11) having a factor of three in the numerator was used. It is determined from the simulation work presented here that Eq. (11) is a more accurate estimate of the lower limit detection in dPCR. A total volume of 5 µL is chosen for these simulations. Then the minimum detectable concentration is 2000 mol/mL. The maximum detectable concentration is essentially determined by the volume of the smallest well $V_0$ in both types of arrays. In particular, for the uniform array:

$$C_{max} = \frac{1}{V_0}\ln[N/3] \quad (18)$$

For the multivolume array this becomes:

$$C_{max} = -\frac{1}{V_0}\ln[1 - (0.05)^{1/2M}] \quad (19)$$

Hence it can be seen that the dynamic range $C_{max}/C_{min}$ is roughly given by the ratio of the total volume to the volume of the smallest well in the array.

The designs of the well arrays in this study are chosen to have the same total volume of $V_{TOT}$=5 µL and a dynamic range of $10^5$. Specifically they can measure concentrations in the range of $C_{min}$=2000 mol/mL to $C_{max}$=2×10$^8$ mol/mL. For the uniform volume array:

$d_0$=40 µm $N$=100,000 $\quad (20)$

For the multivolume array:

$d_0$=25 µm $N$=100

$M$=10

$\delta$=2 µm $\quad (21)$

It is noted that the multivolume array has a total of 2020 wells, which is just 2% of the number of wells in the uniform array. The total area (footprint) of the multivolume array is 100 mm$^2$ compared to the much larger area of the uniform array of 450 mm$^2$.

The simulation of dPCR experiments in these two arrays has been performed using MATLAB. The filling of the arrays with a template of a given concentration λ mol/mL is achieved using a Monte Carlo approach. The Poisson probability that k molecules is loaded into a well of volume V is given by:

$$p(k) = \frac{(V\lambda)^k \exp(-V\lambda)}{k!} \quad (22)$$

However one only needs to keep track of which wells are empty after filling. This corresponds to the case of k=0 in Eq. (12). Then for each well in the array a random number x on the interval [0, 1] is chosen and the following test is applied to determine if the well is empty:

$$x < \exp(-V\lambda) \quad (23)$$

Let b be the number of wells that are empty. For the uniform volume array the measured concentration is simply:

$$C = \frac{1}{V_0}\ln(N/b) \quad (24)$$

For the multivolume array we determine the number of empty wells $b_n$ for each group of wells in the array that have volume $V_n$. Then the measured concentration is found by solving the functional equation:

$$V_{TOT} = 2M \sum_{n=0}^{N} V_n = \sum_{n=0}^{N} \frac{(2M - b_n)V_n}{1 - \exp(-CV_n)} \quad (25)$$

Figure 17B:
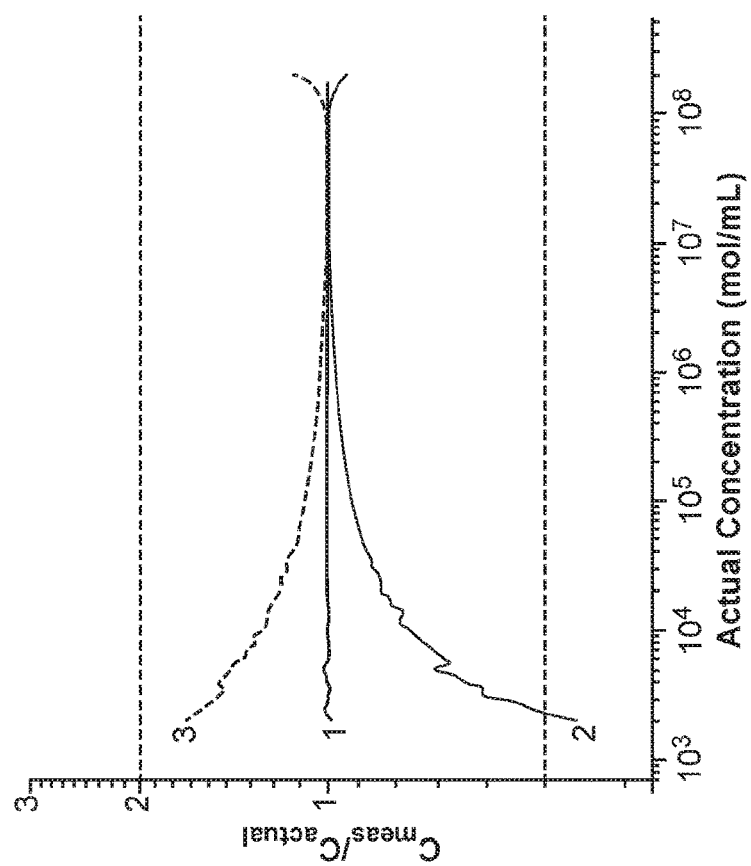
FIG. 17 depicts simulation of the dPCR measurement for the uniform volume array. The middle line is the mean measured concentration. The top and bottom lines define the 95% confidence band of the measurement. The right-side plot shows the measured concentration values normalized to the actual concentration. The dashed lines define the region where the measurement is within a factor of two of the actual concentration.
Figure 17A:
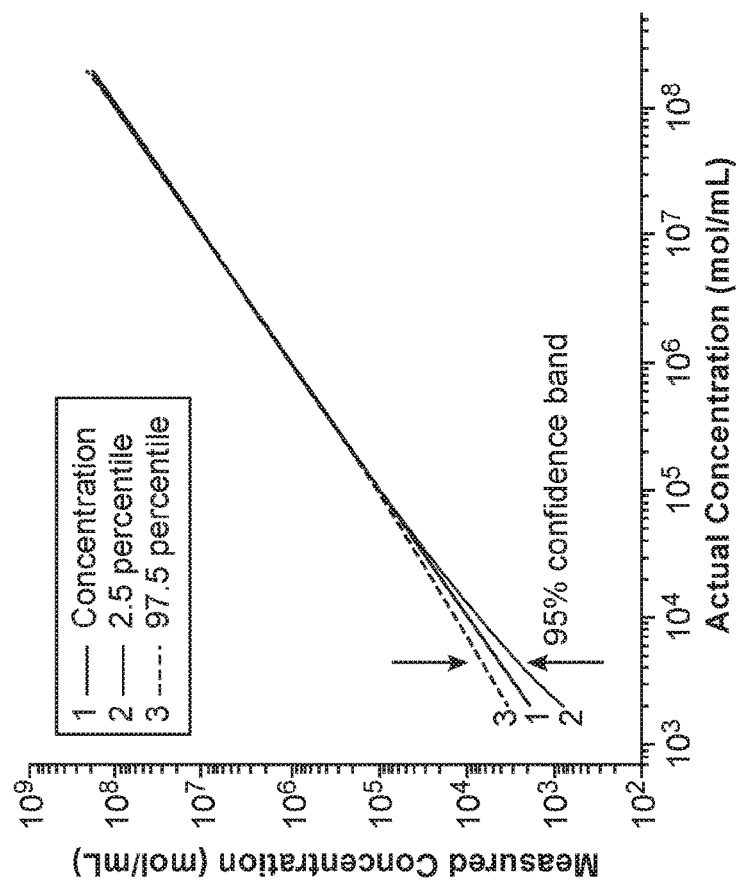
Figure 18B:
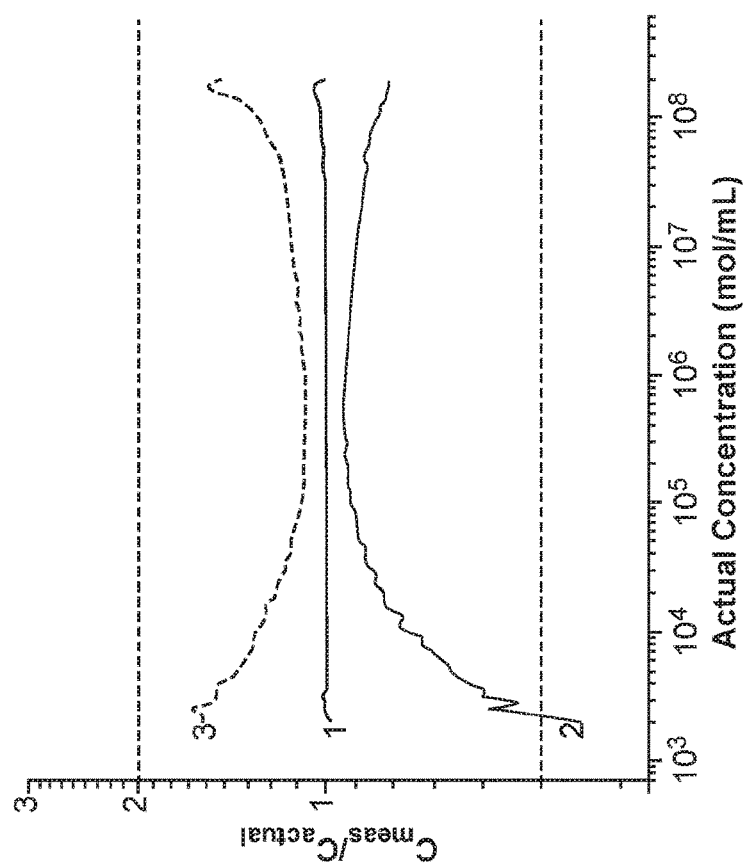
FIG. 18 depicts simulation of the dPCR measurement for the multivolume array. The middle line is the mean measured concentration. The top and bottom lines define the 95% confidence band of the measurement. The right-side plot shows the measured concentration values normalized to the actual concentration. The dashed lines define the region where the measurement is within a factor of two of the actual concentration.
Figure 18A:
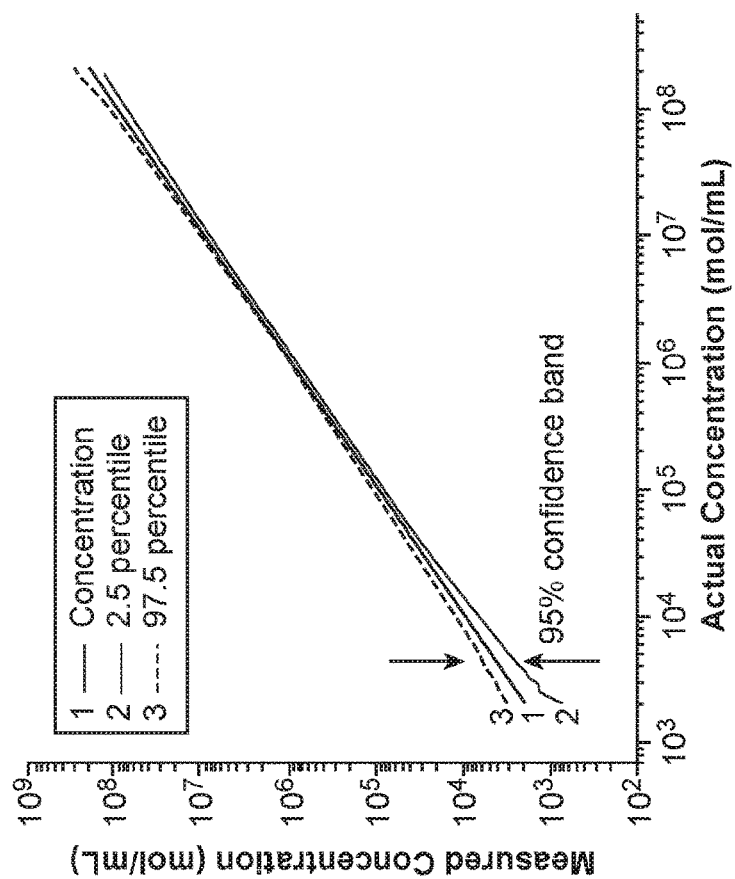

The dPCR simulation was performed for 100 values of template concentration over the range from $C_{min}$ to $C_{max}$. The measurement was repeated 1000 times at each concentration value to derive a statistical distribution of values. The mean measured concentration and the 95% confidence band corresponding to the range of measured values between the 2.5% and 97.5% percentiles of the distribution are reported. The results for the uniform volume array and multivolume array are shown in FIG. 17 and FIG. 18, respectively. The middle line in the plots is the mean measured concentration. The top and bottom lines define the 95% confidence band of the measurement. The right-side plot in each figure shows the measured concentration values normalized to the actual concentration. The dashed lines define the region where the measurement is within a factor of two of the actual concentration.

It is evident that the performance of the two arrays is quite similar. The mean measurements of concentration are very accurate over the entire dynamic range of $10^5$. The width of the confidence band increases at the lower concentration end of the dynamic range for both arrays, so that the precision of the measurement is only within a factor of two of the actual concentration near the minimum detectable concentration. The confidence band for the uniform volume array is narrower than that of the multivolume array at the higher concentrations. However the precision is still adequate for the multivolume array, considering that it has only 2% of the number of wells of the uniform array.

As used herein, the singular terms "a," "an," and "the" include plural referents unless the context clearly dictates otherwise. Thus, for example, reference to a molecule can include multiple molecules unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. A device comprising a microfluidic chip which defines a microwell having a volume less than about one microliter and a channel in communication with the microwell, an imaging system configured to image the microwell, and an acoustic transducer positioned with respect to the microwell to apply in a contactless manner an acoustic beam to the microwell, and wherein the acoustic transducer is not integrated within the microfluidic chip.

2. The device of claim 1, wherein the microwell has a volume configured to receive a single cell or other biomolecules or particles.

3. The device of claim 1, wherein the microwell has a volume of about one nanoliter or less.

4. The device of claim 1, wherein the microfluidic chip comprises at least about 1000 microwells.

5. The device of claim 1, further comprising an actuator configured to translate the microfluidic chip laterally or vertically with respect to the acoustic transducer.

6. The device of claim 1, wherein the acoustic transducer is configured to operate at a frequency of about 1-50 MHz.

7. The device of claim 1, wherein the acoustic transducer is configured to apply a focused acoustic beam on a spot having a size of about 25-200 μm within the microwell.

8. The device of claim 1, the acoustic transducer is configured to apply an acoustic beam to the microfluidic chip via a coupling medium.

9. The device of claim 8, wherein the coupling medium comprises water.

10. The device of claim 1, wherein the microfluidic chip comprises an aqueous compartment comprising a cell or a biomolecule disposed in the microwell, and a non-aqueous liquid phase immiscible with the aqueous compartment disposed in the channel which encapsulates the aqueous compartment in the microwell.

11. The device of claim 10, wherein the microfluidic chip comprises an aqueous compartment comprising a nucleic acid or a protein disposed in the microwell and is substantially free of cells.

12. The device of claim 10, wherein the acoustic transducer is configured to apply a focused acoustic beam to displace the interface of the aqueous compartment and the non-aqueous liquid phase.

* * * * *